(12) United States Patent
Nace

(10) Patent No.: US 7,963,933 B2
(45) Date of Patent: Jun. 21, 2011

(54) OSTEOARTHRITIS KNEE ORTHOSIS

(76) Inventor: Richard A. Nace, San Jose (CR)

( * ) Notice: Subject to any disclaimer, the term of this patent is extended or adjusted under 35 U.S.C. 154(b) by 552 days.

(21) Appl. No.: 12/099,997

(22) Filed: Apr. 9, 2008

(65) Prior Publication Data

US 2009/0259154 A1    Oct. 15, 2009

(51) Int. Cl.
*A61F 5/00* (2006.01)
*A61F 5/34* (2006.01)

(52) U.S. Cl. .............. 602/26; 602/13; 602/16; 602/23; 128/118.1; 128/882

(58) Field of Classification Search .............. 602/16, 602/23, 5, 13, 26; 601/5; 128/118.1, 882
See application file for complete search history.

(56) References Cited

U.S. PATENT DOCUMENTS

| | | | |
|---|---|---|---|
| 3,581,741 A | 6/1971 | Rosman | |
| 4,865,024 A | 9/1989 | Hensley et al. | |
| 4,966,133 A | 10/1990 | Kausek | |
| 4,991,571 A * | 2/1991 | Kausek | 602/16 |
| 5,230,695 A | 7/1993 | Silver et al. | |
| 5,360,394 A | 11/1994 | Christensen | |
| 5,385,538 A | 1/1995 | Mann | |
| 5,458,565 A | 10/1995 | Tillinghast, III et al. | |
| 5,462,517 A | 10/1995 | Mann | |
| 5,514,081 A * | 5/1996 | Mann | 602/20 |
| 5,520,622 A | 5/1996 | Bastyr et al. | |
| 5,527,268 A | 6/1996 | Gildersleeve et al. | |
| 5,542,911 A | 8/1996 | Cassford et al. | |
| 5,792,084 A | 8/1998 | Wilson et al. | |
| 5,865,166 A | 2/1999 | Fitzpatrick et al. | |
| 6,010,474 A | 1/2000 | Wycoki | |
| 6,309,368 B1 | 10/2001 | Herzberg et al. | |
| 6,669,660 B2 | 12/2003 | Branch | |
| 6,740,054 B2 * | 5/2004 | Stearns | 602/16 |
| 2005/0004499 A1 | 1/2005 | Bauerfeind et al. | |
| 2005/0192522 A1 * | 9/2005 | Houser | 602/16 |
| 2006/0200057 A1 | 9/2006 | Sterling | |

* cited by examiner

*Primary Examiner* — Patricia M Bianco
*Assistant Examiner* — Keri J Nelson
(74) *Attorney, Agent, or Firm* — James E. Larson

(57) ABSTRACT

An osteoarthritis knee brace includes at least one vertical strut with upper and lower portions, at least one pivoting hinge intermediately disposed there between, a shin cuff attached to the vertical strut lower portion and positioned below the hinge and a thigh cuff attached to the vertical strut upper portion and positioned above the hinge. The brace further includes at least one inflatable bladder system for applying a corrective and therapeutic force to the osteoarthritis damaged knee joint and the surrounding areas thereof, and which is removeably positionable thereabout. Still further, the brace includes at least one insert enclosed within the inflatable bladder system for equally distributing the corrective and therapeutic force at each point at which the inflatable bladder system applies a corrective and therapeutic force.

36 Claims, 24 Drawing Sheets

OSTEOARTHRITIS KNEE ORTHOSIS

FIELD OF THE INVENTION

The invention relates to osteoarthritis knee orthosis. More particularly, it refers to osteoarthritis knee orthosis for unloading and stabilizing a compartmentally damaged knee joint and for applying adjustable corrective and therapeutic force, which operates to correct abnormal gait and to rehabilitate the knee joint and surrounding muscles above and below the knee by recruiting said muscles.

BACKGROUND OF THE INVENTION

Orthotic devices and appliances commonly referred to as "orthotics," are known in the prior art and have been utilized for many years by orthotists (a maker and fitter of orthotics), physical therapists, and occupational therapists to assist in the rehabilitation of a patient's joints and associated limbs or adjacent skeletal parts of the patient's body related to a condition known as osteoarthritis. Such early devices can be seen in U.S. Pat. No. 3,581,741 to Rosman, which discloses a knee brace comprising an upper rigid body portion and a lower rigid body portion pivotably coupled together on the lateral side in a manner so that they may pivot relative to each other about an axis generally perpendicular to the zone of overlap and may slide relative to each other in all radial directions generally parallel to the zone of overlap. In this application the words osteoarthritis knee orthosis is interchangeable with the term osteoarthritis knee brace.

Webster's New College Dictionary defines "orthotics" as a branch of mechanical medical science that deals with the support and bracing of weak or ineffective joints or muscles. The word "ortho" actually comes from Greek and means "to straighten." Orthotics are used to support and straighten the effected joint and assist to correct normal human function as closely as possible. Orthotics used as limb braces have typically been designed to support and protect the joint that is associated with osteoarthritis, for alleviating pain associated with joint movement at the particular location being treated.

Primary osteoarthritis is typically related to the simple fact of aging and most often affects weight bearing joints, such as the knee. With aging, the water content of the cartilage between two bones in a joint tends to increase, whereby the protein makeup of the cartilage degenerates, which then causes it to become soft, frayed and thinned with eburnation of the subchondral bone. Repetitive use of a joint, such as the knee, over the years, which by the way is simply unavoidable and in fact is wholly necessary for normal human function, irritates and inflames the cartilage, thereby causing joint pain and swelling. Eventually, cartilage begins to degenerate by flaking or by forming tiny crevasses there within. In advanced cases, there is a total loss of the cartilage cushion between the femur and tibia bones at the knee joint, leading to diminished joint space on one or more affected sides of the knee resulting in pain and limitation of joint mobility. Inflammation of the cartilage can also stimulate new bone outgrowths (also known as "bone spurs") to form around the joints causing increased pain and further joint inflammation thereby exacerbating the condition to a point where many people can barely walk, or if do so, is done with an extreme amount of pain.

Osteoarthritis is often described as "wear and tear" arthritis, as it is highly correlated to the age of a person. Osteoarthritis is one of the most frequent causes of physical disability among adults. More than 20 million people in the United States have the disease. By 2030, it is estimated that 20 percent of all Americans, approximately 70 million people, will have passed their $65^{th}$ birthday and will be at risk for osteoarthritis. Other names for this disease are known as degenerative arthritis, degenerative joint disease, osteoarthrosis and arthrosis 2.

When referring to osteoarthrosis, it is generally accepted that it is a condition of degeneration of the effected joint. Osteoarthritis implies the same meaning, but the "itis" adds the meaning that the joint is inflamed. However, the two terms are often used interchangeably and can, should and will, for the purposes of the novel invention described hereinafter, be so interchangeably used.

Joint replacement surgery of the knee is the surgical treatment for osteoarthrosis or osteoarthritis. Most practitioners will recommend that it is best to delay knee joint replacement surgery as long as possible, as a total knee replacement may then need to be replaced in another ten to twenty years thereafter. Further, joint replacement surgery is a major surgical procedure, which requires considerable rehabilitation therapy to restore full function thereafter and full anesthesia during the surgical procedure. Joint replacement surgery should be a choice of last resort.

Surgical correction is very effective in alleviating the pain associated with knee OA and returning the patient's gait to a more normal walking pattern. However, as noted above, the surgery is expected to last only about 10 to 20 years because of the typical life of the artificial components used to correct the knee joint. As such, younger patients are often not considered good candidates for this surgery. Other OA patients simply cannot afford total knee replacement surgery and may be poor candidates for other health reasons. These patients badly need new technology in OA bracing that provides rehabilitation of the OA knee and a delay to OA progression.

Exercise, weight loss, if needed, and the use of anti-inflammatory medications and analgesics are often first prescribed to assist the patient in managing the pain associated with osteoarthritis. In more advanced cases though, steroids may be employed. Regardless of the care chosen or employed, minimizing the progression of the damage to the cartilage of the knee joint and preventing the formation of bone spurs from "bone-on-bone" contact during knee joint flexion should be an important part of any and all patient care.

The actual pain of osteoarthritis or osteoarthrosis of the knee comes from a wearing away of the soft cartilage that pads the junction of the femur (upper leg bone of the knee) and the tibia (lower leg bone of the knee). With irritation of the joint, bone spurs can form causing bits of bone and cartilage to break off which float inside the joint space further irritating the knee and causing addition discomfort and paid.

The most common form of osteoarthritis or osteoarthrosis is unicompartmental, meaning that only one of the three compartments of the knee joint are significantly affected by the loss of the cartilage padding. When speaking of a "compartment of the knee," it is meant to be the area that is a separate section or chamber between the end portions of closely juxtaposed bones. In a healthy knee, these "compartments" contain the cartilage and synovial fluid, a thick and stringy fluid that acts as a lubricant in the joint that helps to reduce friction therein.

The "medial compartment" of the knee is on the inside of the center line of the body, whereas, the "lateral compartment" of the knee is on the outside plane of the body. The "patellar compartment" is on the center top of the knee behind the patella or knee cap.

The majority of cases of osteoarthritis of the knee experience medial compartment degeneration wherein the cartilage or cushioning of the knee joint has significantly deteriorated.

The knee then becomes imbalanced, with the knee bowing outwardly. This is often called a "bowlegged" condition or a "varus deformity" of the knee joint, wherein significant force is exerted on the medial compartment of the knee, which then causes significant pain when the patient walks, bends the knee, or stands up. As a result, the patient typically adopts an abnormal gait, which is most often recognized by an exaggerated swinging of the hips. This abnormal gait can progress the osteoarthritis and lead to a more serious condition. Recent studies on the effects of abnormal gait and how it leads to OA progression have recently been conducted and have shown this to be an aggravating factor of OA disease.

Without proper treatment, which should include a corrective and therapeutic force system incorporated into an OA brace to correct an abnormal gait, OA progression in a patient can lead to a pathological OA condition, which will most likely force the patient into the necessary, but highly undesirable and expensive, surgical knee joint replacement. To date, no OA knee braces in the prior art incorporate such a corrective and therapeutic force system; but such a system is clearly needed. Further, "regular" abnormal gait, let alone pathological OA gait, causes an abnormal swinging of the hips and can result in more severe problems for the patient by placing abnormal stress and force on the hip joints, which if left unchecked or untreated will most often lead to a secondary condition for the patient of osteoarthritis of the hip. The patient is essentially doing more damage to the body as a whole by swinging the hips abnormally by rotating or "torquing" the knee joint, or what is also known as a "reverse screw home mechanism."

Besides the physical pain associated with medial compartmental degeneration, OA of the knee can cause the patient to feel awkward, inadequate and embarrassed from this abnormal gait, which can then lead to an even more sedentary and reclusive lifestyle, which can further lead to aggravated psychological conditions, such as depression.

Returning back to the specific causes of an osteoarthritis knee condition, as the cartilage or padding of the knee joint on an effected lateral compartment cartilage is worn away the knee will again deform abnormally, but instead this time it will bend inwards at the knee joint, thereby giving the patient a knock-kneed appearance or a "valgus deformity" of the knee joint.

Osteoarthritis (OA) knee braces are known in the prior art and are primarily designed to do two things. First, correct the abnormal bending of the knee joint inwards or outwards (i.e., varus or valgus correction). Secondly, most OA knee orthotics or braces are designed to prevent the "bone-on-bone" contact of the femur and tibia bones in the medial and/or lateral compartment of the knee joint as the patient bares weight during ambulation. This action of lifting the femur, pulling down the tibia or keeping the femur and tibia bones from coming in contact during the straightening of the knee during heel strike of the foot is often called "unloading" of the knee joint, which is known to be only a temporary relief from pain by those stricken with such disease. By unloading the knee joint, the constant irritation of the degenerated cartilage in the effected compartment of the knee (medial or lateral) can lead to a reduction in pain and a further reduction in injury to the knee joint.

Prior art osteoarthritis knee braces also provide improved alignment of the upper and lower aspects of the knee joint by preventing the bending inwards or outwards of the knee joint during gait. These two features, unloading and alignment, are provided by almost all osteoarthritis knee orthotics available in today's market and those products that are known in the prior art. When these prior art braces are removed however, little or no rehabilitation of the knee occurs and a return of the pain without brace use is apparent. This reinforces the fact that prior art "unloading" braces lack any significant rehabilitative components, which could actually strengthen the leg and improve the knee joint balance to delay the progression of OA and to improve the patient's condition when the brace is not being worn.

Further, none of the OA braces in the prior art work to correct walking gait kinetics to an actual or more "normal gait." In fact, while the prior art devices may assist in straightening the leg somewhat, the patient will still be seen striking the foot along an outside edge on a varus deformity (bowlegged) condition and on an inside edge on a valgus deformity (knock-kneed) condition. This is because none of the prior art devices use a corrective and therapeutic force system in coincidence with the OA brace to return the patient to a true, more normal gait wherein actual heel-to-toe striking along the ground surface is realized along with a lengthening of the leg step. Further, none of the prior art devices use a corrective and therapeutic force system in combination with a swing-assist system that forces activation of atrophied muscles, such as the quadriceps, which actually rehabilitates the effected area and encourages these atrophied muscles, through recruitment, to begin to work again, thereby assisting the patient to return to the closest, more normal gait as possible based upon the severity and progression of their specific disease condition. None of the prior art OA braces actually rehabilitate and strengthen the leg musculature, with any significance, such that after several months of routine brace use, there is a significant less amount pain when walking or standing or when not using the brace as compared to the pain experienced prior to brace use.

Further, a majority of knee orthotics available to treat osteoarthritis of the knee utilize a single upright attached to an upper thigh cuff and lower shin cuff. The upright is located on the side of the collapsed compartment of the knee (i.e., medial side for medial compartment osteoarthritis or lateral side for lateral compartment osteoarthritis). The attached cuffs "unload" the biomechanical force on the effected compartment of the knee by increasing the joint space on the effected side as the knee goes from flexion to extension.

Many known osteoarthritis knee braces use an angled strap from the upper part of the brace that then goes across the opposite side of the knee joint from the single upright to the lower part of the brace to improve the alignment of the knee during ambulation to and better balance the forces on the knee during gait kinetics more evenly. Such a brace can be seen with the devices marketed by the company ÖSSUR. The strap provides a three point leverage system that attempts to pull the knee joint into proper alignment during gait. A combination of the single sided upright with cuff attachments and the valgus producing strap have shown to provide improved performance in severe genu varum osteoarthritis. However, it is difficult to set the desired degrees of flexion and extension in such devices and therefore these devices are known to fall short of providing a close-to-complete alleviation of the pain and discomfort from osteoarthritis and a return to normal walking gait, let alone providing any a corrective and therapeutic force system to rehabilitate the effected knee joint and surrounding muscles. Further, patient discomfort and brace slippage is a real and common problem with braces designed as such.

Other known brace designs employ a double upright strut, which merely immobilizes the knee by unloading the degenerative knee compartment and thereafter doing nothing more. In some prior art devices, non-slippage and comfort pads are employed along inner lateral surfaces of said upright struts.

However, none of these prior art devices disclose, teach or suggest the use of cushion pads, let alone inflatable or pneumatic bladders to apply an additional corrective or therapeutic force to rehabilitate the knee joint and surrounding muscles through forced work and recruitment. Still further, none disclose a system that works in coincidence with the corrective or therapeutic forces to equally distribute said forces.

There is also a need to provide a swing-assist activity to patients with either medial or lateral compartmental osteoarthritis. The ÖSSUR devices provide no such function, nor do any other known OA braces in the prior art.

Still further, although many of the existing knee braces containing locking hinge assemblies serve their intended purpose, difficulty in ease of setting the desired degrees of flexion and extension continues to be a problem, which clearly needs improvement.

What is therefore needed is a complete OA knee brace that can unload the knee, stabilize the effected compartment, provide a swing-assist function for extension of the knee, provide a corrective and therapeutic force that can return the patient to a more true normal gait (heel-to-toe strike while walking) and prevent abnormal rotation of the knee joint, all the all the while recruiting atrophied muscles to work again and to rehabilitate themselves so that the patient can once again return to the closest possible "normal" condition based upon the specific progression of their respective disease condition. The goal for any advancement in the art should be an improvement from "abnormal OA gait" to a more biomechanically correct normal gait kinetic, which reduces the knee adduction movement believed to be a casual but significant factor in OA knee compartment degeneration. A truly rehabilitative OA knee brace would strengthen the leg musculature and improve knee joint space balance over time using dynamic adjustable components such that a reduction in pain over time, with and without brace use, would be both evident and realized. Such a described and needed brace currently does not exist in anywhere in the prior art. Simply put, an improved OA knee brace should be used with patients who can begin "brace therapy" prior to OA becoming too severe to effectively improve the condition and thereby avoid pathological OA.

SUMMARY OF THE INVENTION

The present invention provides an osteoarthritis (or "OA") knee orthosis (or "knee brace") easily fabricated in a wide range of sizes for either the left or right knee to treat either medial or lateral (varus or valgus) compartmental degeneration of the knee joint caused by osteoarthritis or osteoarthrosis. Such a novel brace of the present invention provides easily managed controls for setting the desired degree of flexion and extension. The knee orthosis of this invention will unload the pressure on the effected side of the knee joint, provide balanced joint space on both sides of the knee during ambulation, improve knee joint alignment, and all the while be adjustable as the condition of the knee improves or deteriorates to maintain joint space balance and an unloading effect on the damaged knee joint and thereby improve knee joint alignment during gait.

As alignment of the knee changes (joint space balance changes), the knee brace of the present invention can be adjusted so that joint space balance is continually maintained along with joint rehabilitation. The current invention in one embodiment achieves this significant improvement with an adjustable dynamic fulcrum, positioned on the opposing side of the degenerated compartment, to allow the clinician to quickly and easily adjust the brace to maintain joint space balance of the overall knee as needed during the knee rehabilitation process.

The present invention accomplishes the desired result of joint space balance by utilizing a polycentric hinge and a uni-centric hinge component, which are positioned either laterally and medially or vice versus, depending on which side of the knee is damaged, adjacent the knee joint. A semi-rigid cuff is circumscribable about the front of the lower leg. The lower member of each hinge is attached to a lateral and medial upright element integrally attached to the semi-rigid cuff. A semi-rigid thigh cuff is aligned with the back of a patient's thigh, above the knee joint. The thigh cuff has a lateral and medial element extending downwardly to engage a top hinge arm of each hinge. One hinge arm is longer than a corresponding other hinge arm, with the longer hinge arm employed on the knee joint's damaged side. The longer top hinge arm is fixed at a posterior angle of about 10° to 20° in full knee extension. A spring or elastic banded adjustable fulcrum polycentric hinge component is used to assist leg extension-flexion during walking, squatting and sitting. By repositioning a plurality of setting blocks, different degrees of tension can be introduced into the polycentric hinge element. The adjustable fulcrum is a rehabilitative mechanism for the leg musculature that assists in the supporting and surrounding of the knee joint area.

In a preferred embodiment, the OA brace of the present invention provides a system for applying a corrective and therapeutic force to the knee joint area to assist in the traditional functions of an OA knee brace but with the added benefit of actually correcting gait kinetics and preventing abnormal rotation of the knee joint. Therefore, with such a system, a patient with a varus deformity (bowlegged-ness) will realize a significant reduction or elimination of hip abduction, a significant reduction or elimination of varus alignment deformity at the knee joint area, a transformation from an abnormal lateral foot placement walk to a near normal heel-to-toe foot placement and a lengthening of their actual step. Also, in some severe cases, more often seen in valgus deformity (knock-kneed), the patient will realize a near normal gate that eliminates the banging together of the knee joints as one leg swings forward during gait.

This is all accomplished by a novel system that incorporates precisely placed, but adjustable, formed cushions or inflatable or pneumatic bladders that apply the optimal corrective force below and at the knee joint, on both sides thereof, but not above the knee joint, to truly balance the knee joint and reduce the knee adduction moment during gait, which initiates the most damaging torque to the compacted compartment of the effected OA knee. The corrective force system of the novel present invention physically moves the upper and lower segments of the knee in a lateral and/or medial direction depending on the positioning of the corrective force elements of the system. The system allows for the patient to fine tune the OA knee brace by adjusting the corrective force elements since the patient knows what truly hurts, what does not hurt and what a comfortable gait feels like for them.

In addition, the present invention significantly reduces or eliminates "reverse screw home mechanism" or a reversed and abnormal rotation of the knee, which then also reduces the wear and tear damage to the knee joint. This is realized by a posteriorly angled offset at a top end of a longer strut member in a double strut design. In a preferred embodiment, this offset is between 10 and 20 degrees. The corrective force system also contributes to the reduction or elimination of the abnormal rotation of the knee in either the differential length strut design or in an equal double upright strut design of the present invention. These combined innovations in the present invention result in a significant rehabilitation of the knee joint and leg musculature to delay the progression of OA.

Still further, to assist with the comfort level of the brace on the patient and to avoid the brace from slipping or moving when employed, a material having a high coefficient of friction, but which does not cause discomfort against the skin of the patient, is employed along the surfaces of material wraps that surround the hinges and which come in contact with patient's skin.

Still even further, the present invention can be used with a selection of the younger population, who can then rehabilitate OA of the knee and delay the deterioration of OA. Many of these select patients will then be able to extend their ability to realize full mobility for extended periods of time without total knee replacement surgery by simply using the knee brace of the present invention that both unloads the compacted knee compartment and rehabilitates the leg and knee musculature, thereby returning the patient to a more correct walking biomechanic.

Still even further, a pre-operative, post-operative brace utilizing the unique combination of features described above allows for a single patient to use the same OA brace before and after surgery, in those OA cases that require surgery. Nowhere in the prior art does such a brace exist.

BRIEF DESCRIPTION OF THE DRAWINGS

This invention can be best understood by those having ordinary skill in the art by reference to the following detailed description, when considered in conjunction with the accompanying drawings in which.

DETAILED DESCRIPTION OF THE INVENTION

Figure 1:
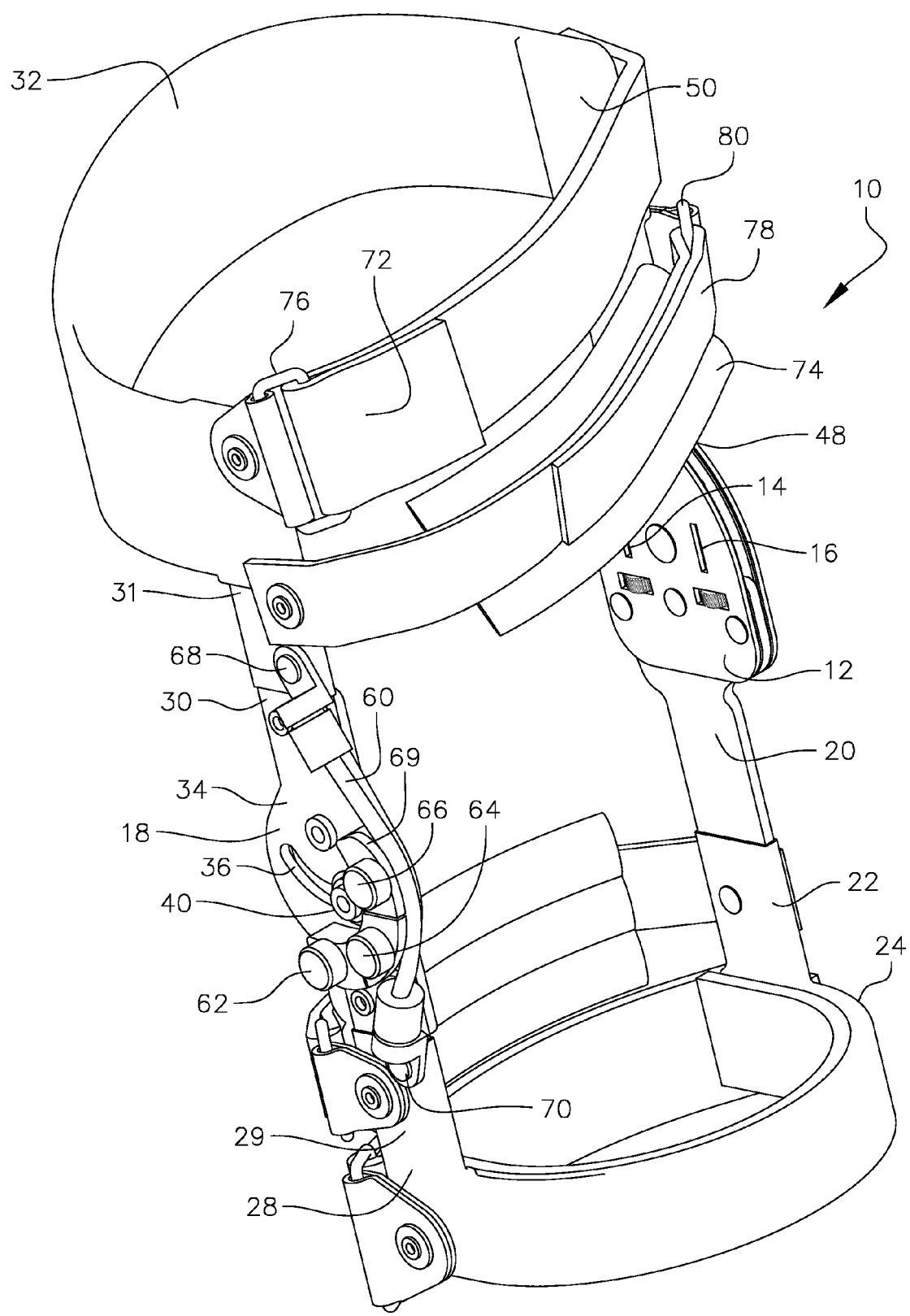
FIG. 1 is a side perspective view of an embodiment of an OA knee brace of the present invention.

Throughout the following detailed description the same reference numerals refer to the same elements in all figures.

Figure 2:
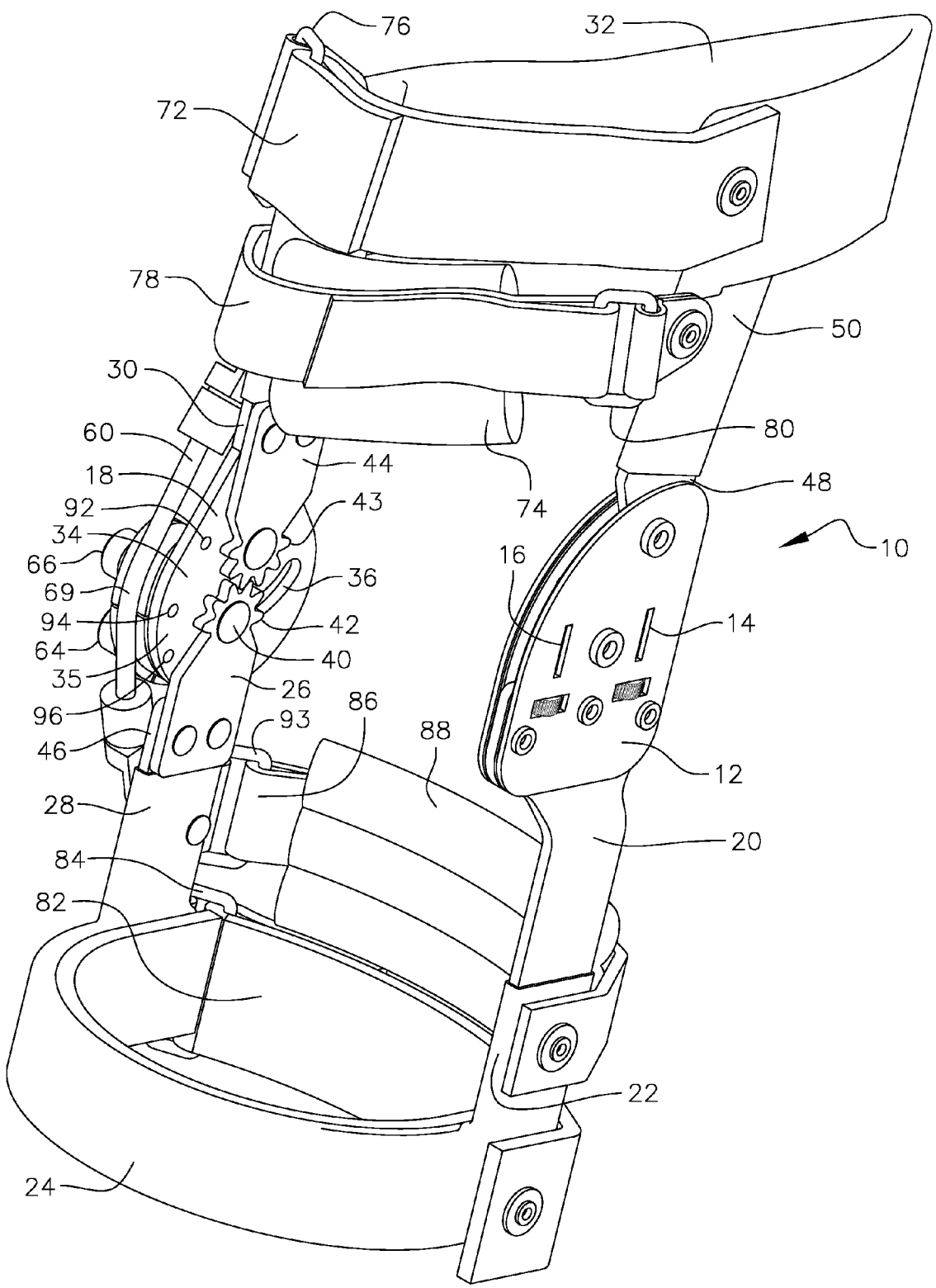
FIG. 2 is side perspective view of the same embodiment of FIG. 1 but shown from an opposed side.

Referring to FIGS. 1 and 2, a first non-preferred embodiment, of an osteoarthritis knee orthosis 10 (also known as an OA brace) is shown. OA brace 10 has a uni-centric hinge 12 with a flexion stop 14 and an extension stop 16, which can be adjusted and set to a plurality of settings, although other uni-centric hinges not employing stops 14 and 16 can be used. Uni-centric hinge 12 is substantially parallel to a polycentric adjustable tension offloading hinge 18. Again, other types of polycentric hinges can be employed for hinge 18 and nothing herein should be construed to limit the present invention of this particular embodiment or the present invention as a whole to that which is shown in FIGS. 1 and 2. For example, two uni-centric hinges or two polycentric hinges could be employed instead of the one of each as shown.

Further to FIGS. 1 and 2, a bottom end 20 of hinge 12 is attached to a first lower upright member 22, which is integral with an anterior shin cuff 24. A lower gear plate 26 (see FIG. 2) of hinge 18 is attached to a second lower upright member 28 integral with shin cuff 24 and positioned below hinge 18.

An upper arm 30 of hinge 18 connects at an upper end 31 thereof to a flexible posterior upper thigh cuff 32. A lower portion of hinge 18 broadens out and contains a slotted hinge connector plate 34. A slot 36 formed in connector plate 34 contains a transverse shaft on a rivet 40. Rivet 40 attaches a first star gear 42 (see FIG. 2) to an inside surface 35 of the slotted connector plate 34. A second star gear 43 is integral with an upper gear plate 44 and attaches to an inner surface 35 of hinge connector plate 34. Other equivalent attachment means could be substituted for rivets 40 to accomplish the same function in the same way in the same manner. Further, although not shown, an identical gear mechanism as used and shown with hinge 18 can also be employed with hinge 12.

An upper arm 48 of hinge 12 extends upwardly and attaches at its top end 50 (see FIG. 2) to the flexible upper thigh cuff 32. Hinge 12, in this embodiment and in the preferred embodiment, is a KWIK-SET™ design as set forth in U.S. Pat. No. 6,039,709, which is incorporated herein by reference. However, other uni-centric hinges 12 can be employed.

As shown in FIGS. 1 and 2, upper thigh cuff 32 is angled and rotated behind the thigh, when employed, to accommodate a double strut differential length by angling downwards from the compartmentally damaged side of the knee to the opposing side and then is rotated inwards at the bottom of thigh cuff 32 (at a lower horizontal plane level) at an angle of approximately 15 to 20° to align with the angle of the upper leg at the back of the lower thigh. This unique arrangement assists in the unloading effected and compacted knee compartment by way conforming to the angle of the lower back of the thigh of the patient, which catches and lifts the inner upper leg area. Nowhere in the prior art can this be found as described herein.

In the embodiment shown in FIGS. 1 and 2, upper thigh cuff angles downward from the medial to the lateral side and the rotation inward at the bottom of thing cuff 32 occurs on the side of hinge 18. However, nothing herein should be construed to mean that the reverse can not be employed. Reversing the angle downward from the lateral to medial side can be employed in the present invention.

Upper portion 48 of hinge 12 is significantly longer than upper arm 30 of hinge 18—about 1 and ½ inches in the medium size in this embodiment. This longer length of upper portion 48 as compared to upper arm 30 translates into the double strut OA brace design, as shown herein, which employs a longer strut on the specific side of the uni-compartmentally damaged knee joint. Therefore, by way of example, in a medial compartmentally damaged knee joint 59, like that shown in FIGS. 3 and 4, the longer strut is placed on a medial side 51 of the knee joint 59 and the shorter strut is placed on the lateral side 53. With close inspection of FIG. 3, it is shown how the medial compartmentally damaged knee joint 59 has no space in a medial compartment 55 between an upper end 56 of a tibia bone 57 and a lower end 52 of a femur bone 54. However, nothing herein limits the brace of the present invention from being an equal double upright strut design or even a single upright strut design.

Figure 3:
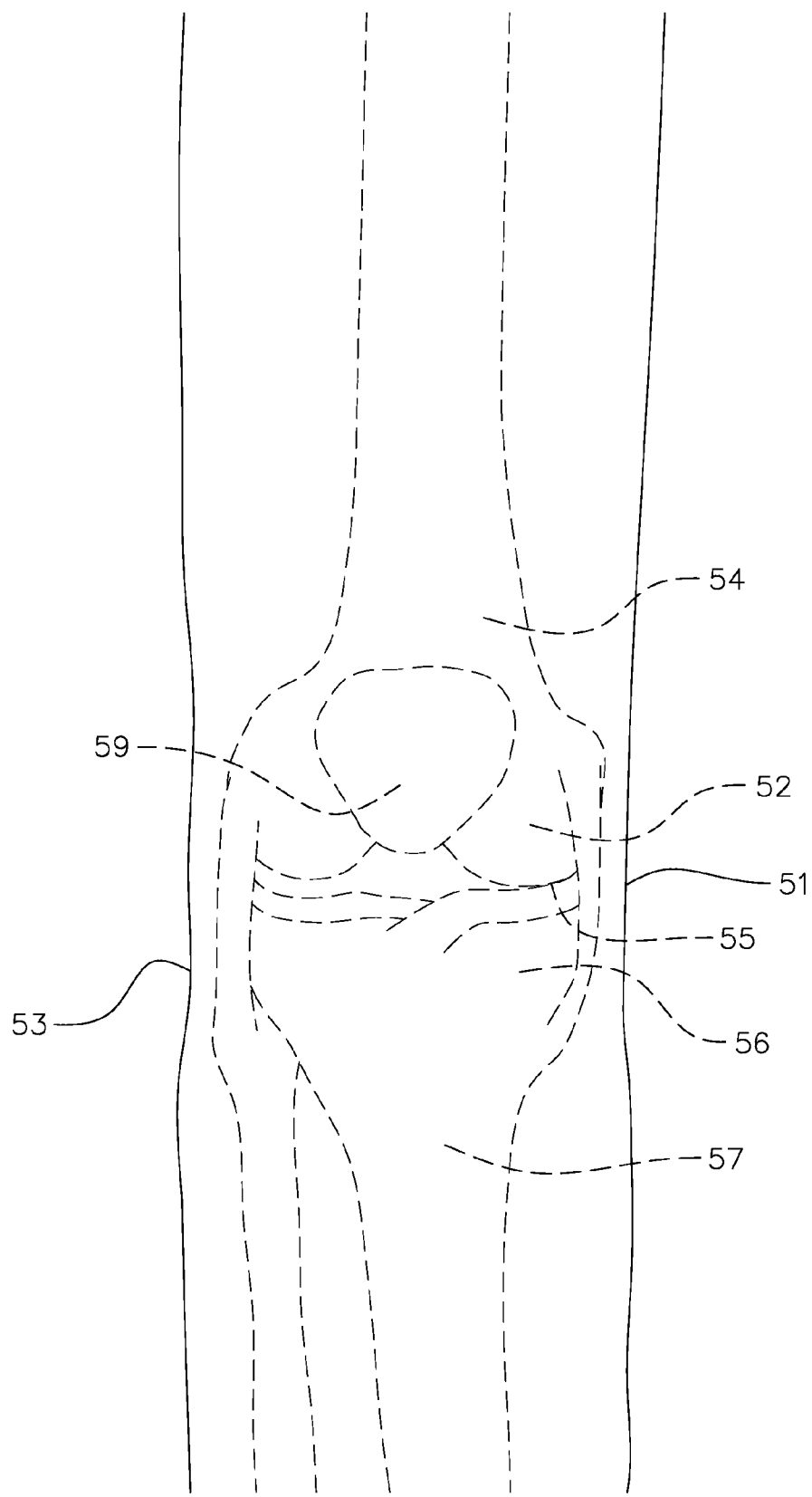
FIG. 3 is a front view of a compartmentally damaged knee wherein the hidden view illustrates said knee being out of alignment.
Figure 4:
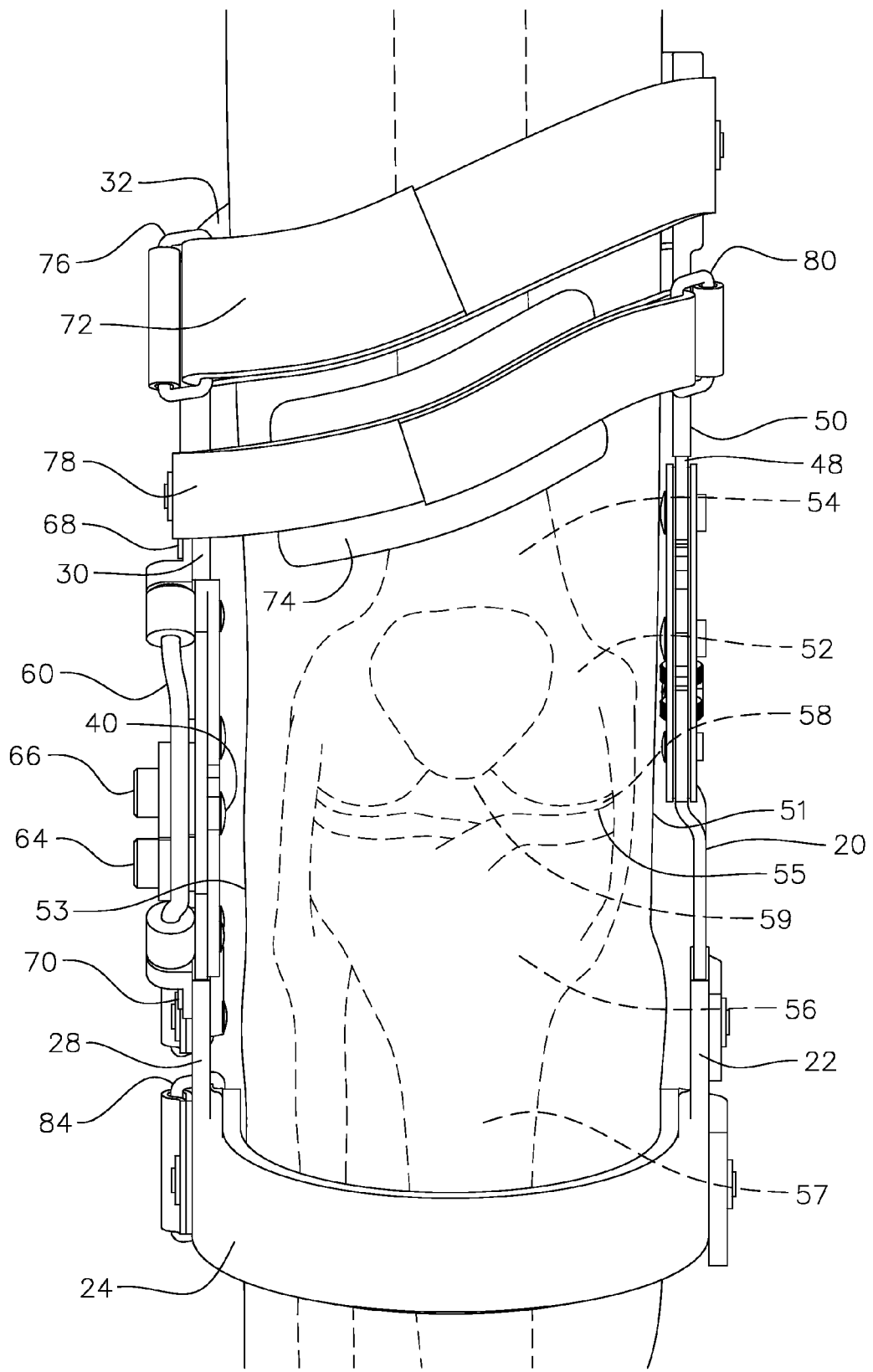
FIG. 4 is a front view of a compartmentally damaged knee wherein the hidden view illustrates said knee being "unloaded" by an OA knee brace of the present invention in one embodiment.

Referring to FIG. 4, with OA brace 10 employed on the knee, it is now shown how the medial compartmentally damaged knee joint 59 is "unloaded" and a space 58 is now formed in medial compartment 55 such that there is no "bone-on-bone" contact of the lower and upper ends, respectively, of the femur 54 and the tibia 57 bones. In particular, the longer length of medial upper portion 48 as compared to that of lateral upper arm 30, encourages the unloading of the force subjected to the medial compartment 55 of the knee by lifting the lower end 52 of the femur 54 on the medial side 51 of the knee off of the upper end 56 of the tibia 57 during a weight bearing action, during full leg extension or during gait kinetics. As further shown in FIG. 4, space 58 is significantly widened when the OA brace 10 is employed, versus the non-existent space as shown in FIG. 3, when OA brace 10 is not employed.

Referring back to FIGS. 1 and 2, first lower upright member 22 and second lower upright member 28 are generally or exactly equivalent in length and generally positioned along a same upwardly extending plane. However, as shown most clearly in FIG. 2, upper portion 48 is set back (or "offset") at an angle of approximately 15° to 20° as compared to first lower upright member 22 when the patient's leg is straight, with hinge 12 positioned in between, whereas upper arm 30 and second lower upright member 28 are in relatively straight alignment with hinge 18 when the patient's leg is straight. The offset position of upper portion 48 improves knee alignment from 20° of flexion to full extension of the knee joint and prevents "reverse screw home mechanism," an abnormal rotation of the knee joint that occurs during gait kinetics because of OA of the knee.

It is understood that FIGS. 1-4 illustrate a medial uni-compartmental damaged right knee joint and the use of OA brace 10 to assist in this condition. However, nothing herein limits the use of OA brace 10 of the present invention for use with a medial uni-compartmentally damaged left knee joint, a lateral uni-compartmental damaged left or right knee joint, or further even a total or bi-compartmental damaged left or right knee joint.

Referring back to FIG. 1, hinge 18 has an elastic band 60, which attaches at a lower end on an outer surface 29 of second lower upright member 28 at a bottom fulcrum point 70 and travels adjacent to a set of adjustable dynamic fulcrum setting blocks 62, 64 and 66 to then terminate at top fulcrum point 68. The dynamic tension of this arrangement creates an adjustable dynamic fulcrum 69 that can be set by an orthosis fitter or by the user themselves, by using fulcrum blocks 62, 64 and 66. In addition, various elastic bands 60 with varying elasticity can be substituted to allow the fitter or user to adjust dynamic fulcrum 69 with a multitude of varying tension forces. Dynamic adjustable fulcrum 69 is derived from elastic band 60 positioned from lower fulcrum point 70 and then stretched over blocks 62, 64 and 66 at hinge 18 as the knee bends, as shown in FIG. 5B. Adjustable dynamic fulcrum 69 is used to provide a dynamic tension force at the knee joint, which assists in balancing the joint space 58 (see FIG. 4) between the medial and lateral compartments and to provide optimal alignment of the knee with the OA brace 10 of the present invention. Elastic band 60 can be substituted with a spring, although not shown.

In the embodiment described so far, adjustable dynamic fulcrum 69 is employed along the polycentric hinge 18 as shown in FIGS. 1-2 and 4 through 8B. However, nothing herein limits the use of adjustable dynamic fulcrum 69 with uni-centric hinge 12.

Figure 5A:
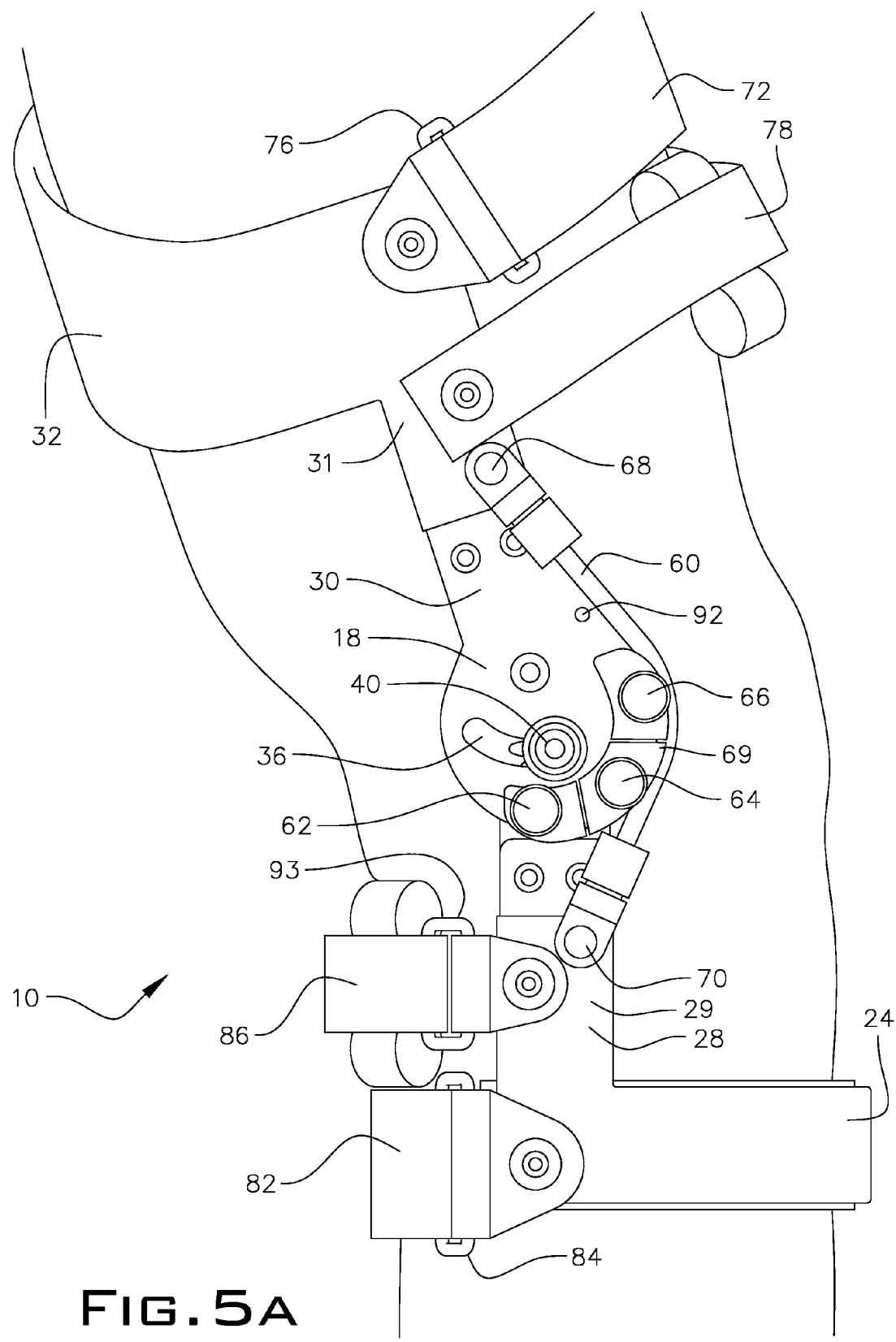
FIG. 5A is side view of a polycentric hinge assembly with dynamic fulcrum employed with the OA knee brace of the present invention, wherein a leg of a patient is extended.
Figure 5B:
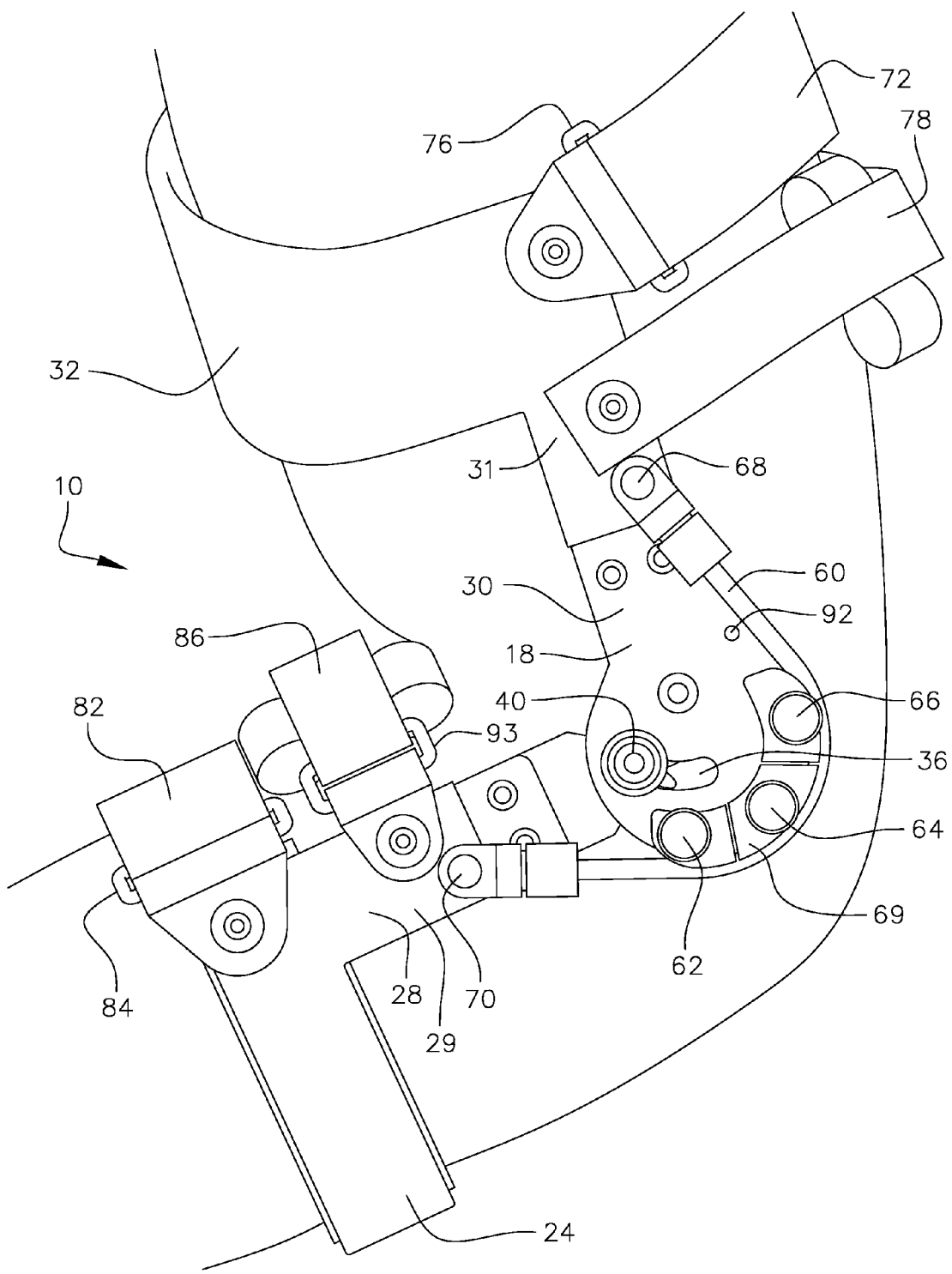
FIG. 5B is side view of the polycentric hinge assembly with dynamic fulcrum employed with the OA knee brace of the present invention, wherein the leg of the patient is in a bent position.
Figure 6A:
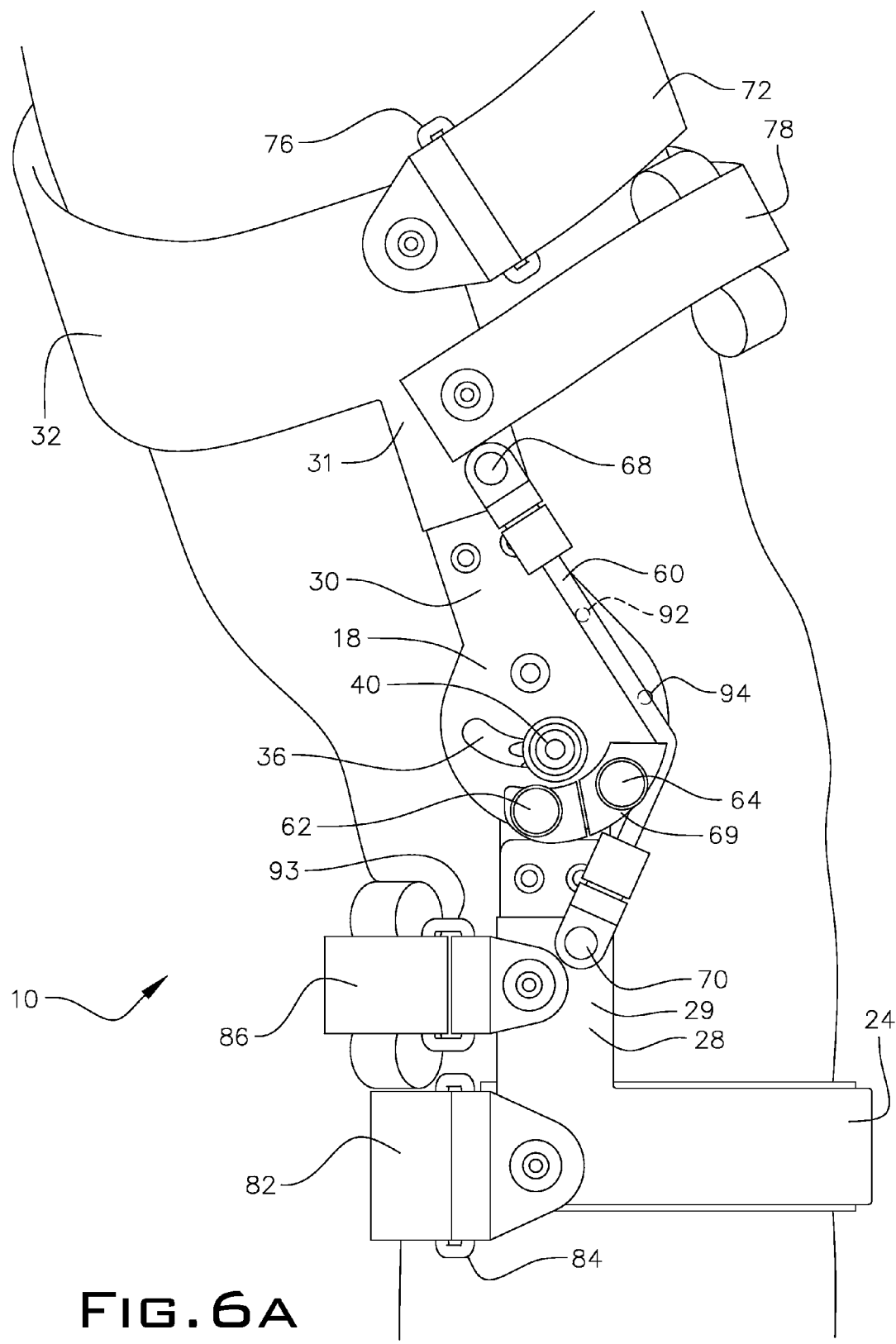
FIG. 6A is a side view of the polycentric hinge assembly with dynamic fulcrum employed with the OA knee brace of the present invention, wherein the leg of a patient is extended and only two setting blocks are employed.
Figure 6B:
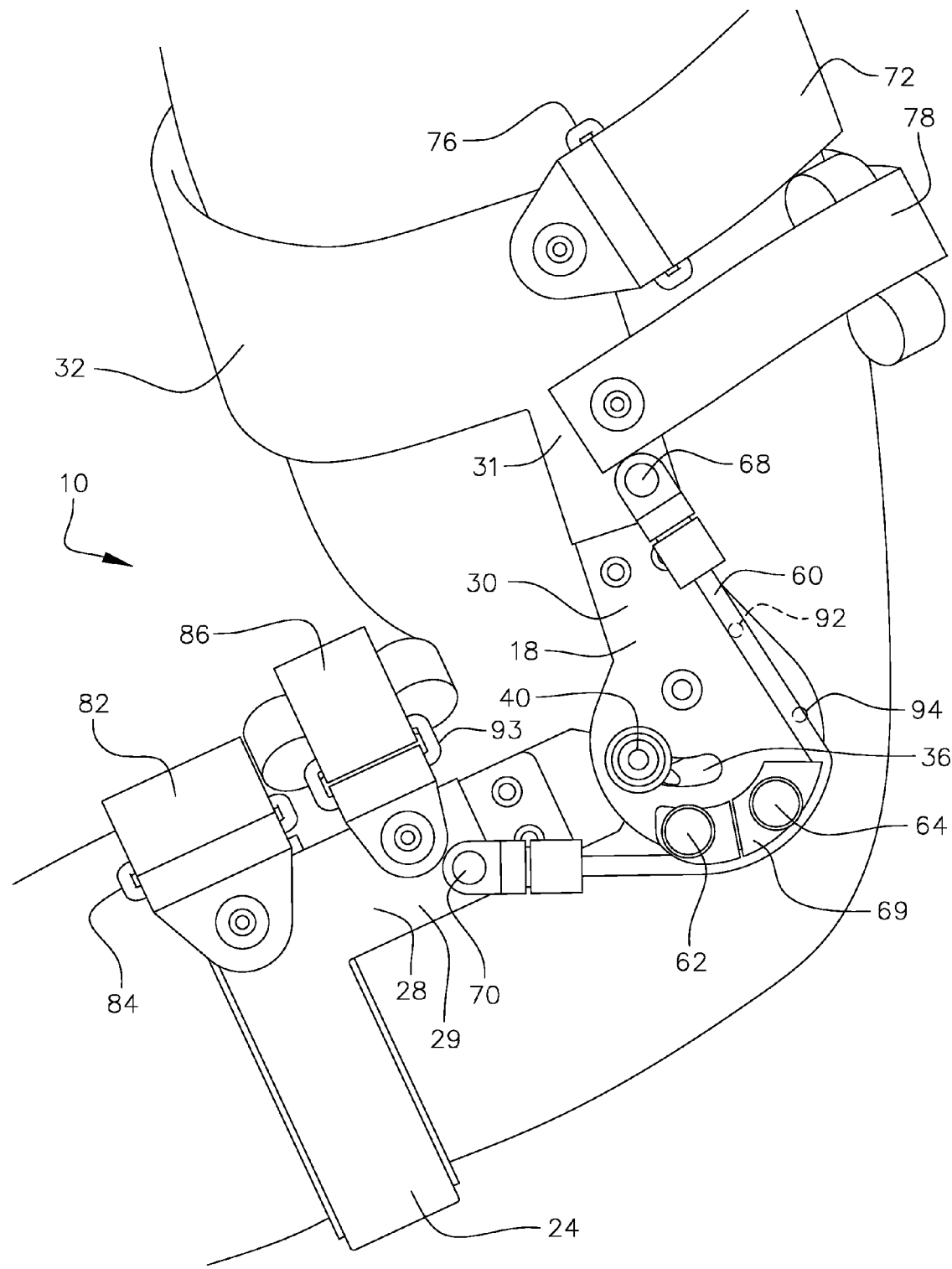
FIG. 6B is a side view according to FIG. 6A with the patient's knee bent.
Figure 7A:
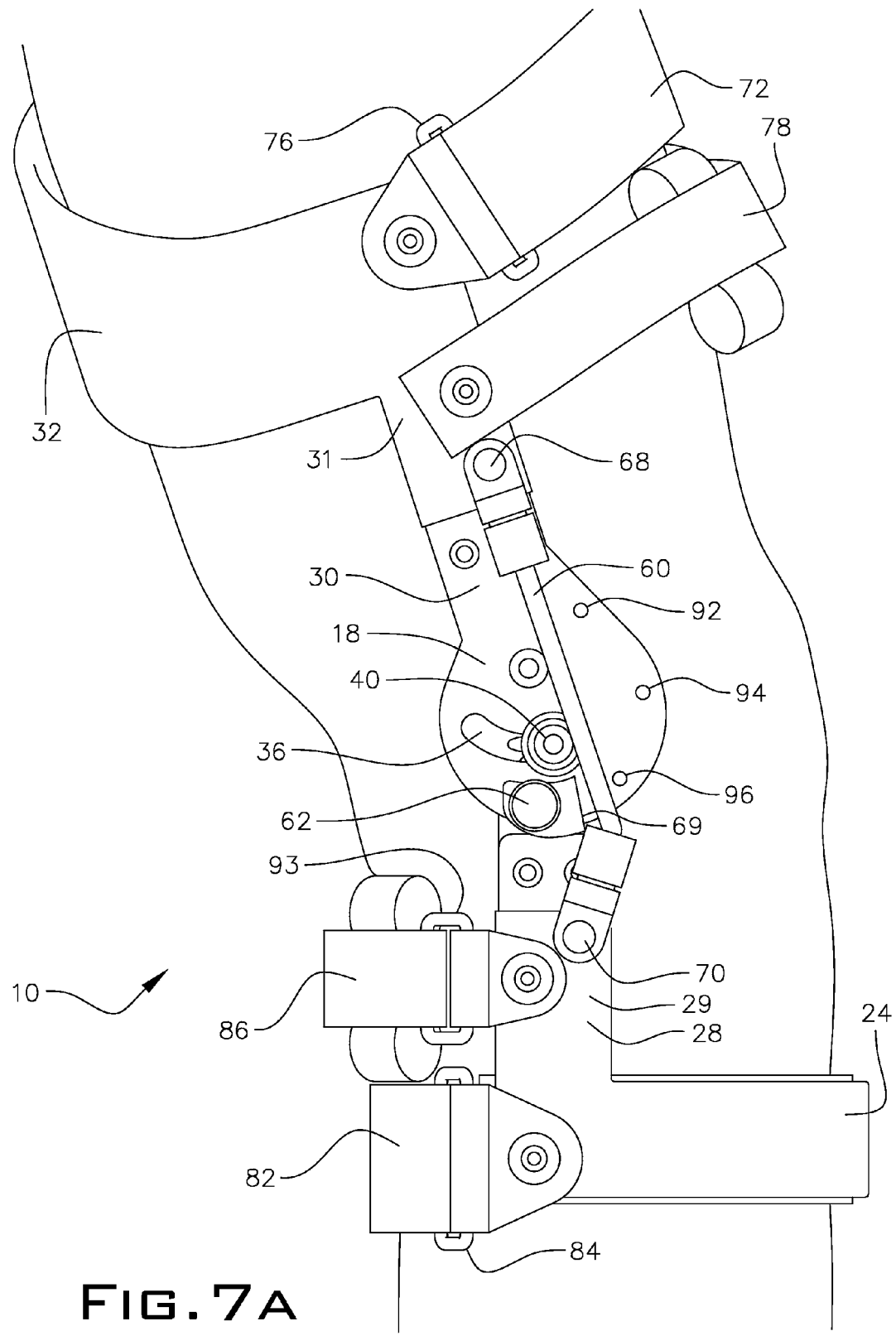
FIG. 7A is a side view of the polycentric hinge assembly with dynamic fulcrum employed with the OA knee brace of the present invention, wherein the leg of a patient is extended and only one setting block is employed.
Figure 7B:
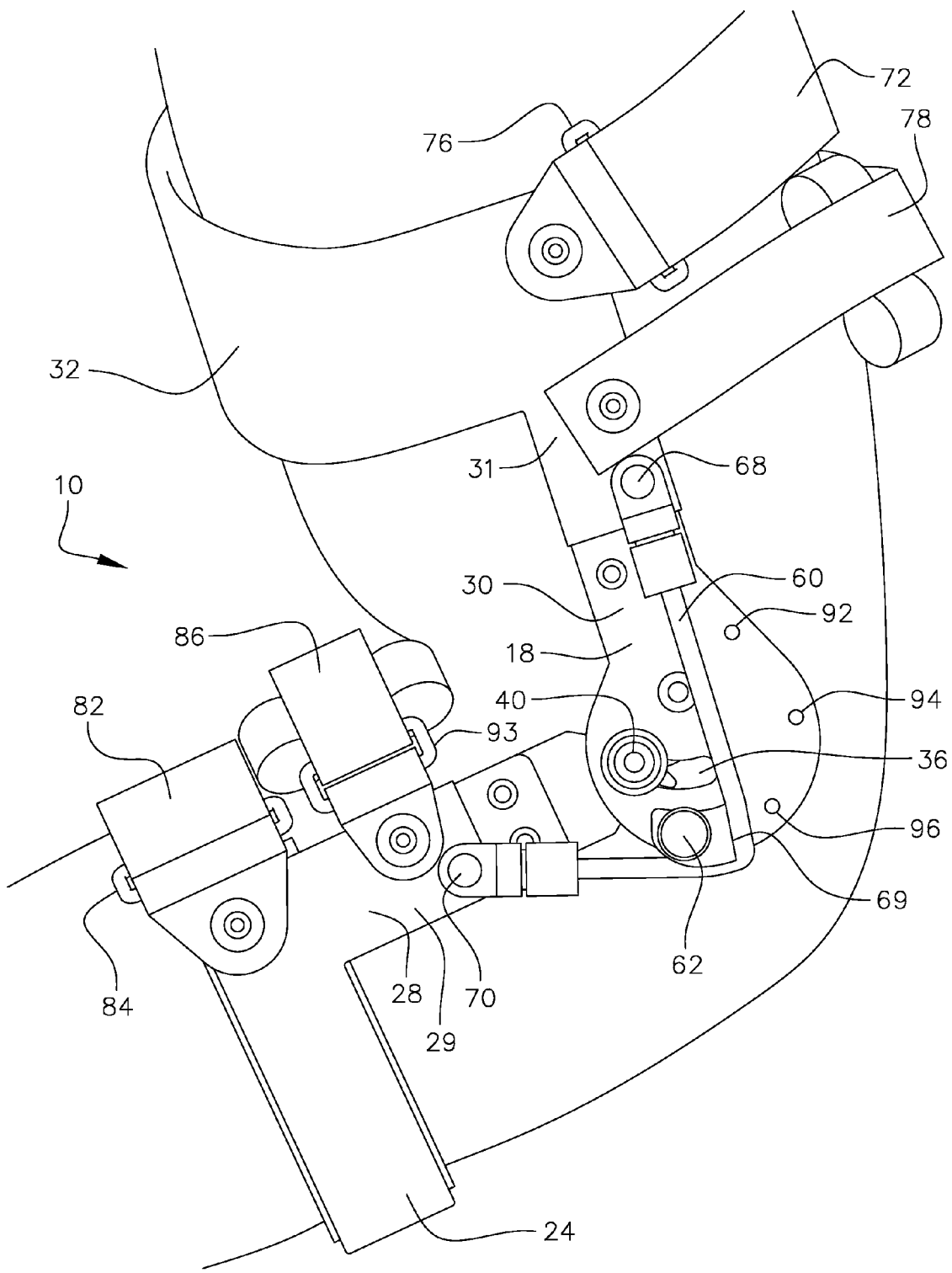
FIG. 7B is a side view according to FIG. 7A with the patient's knee bent.
Figure 8A:
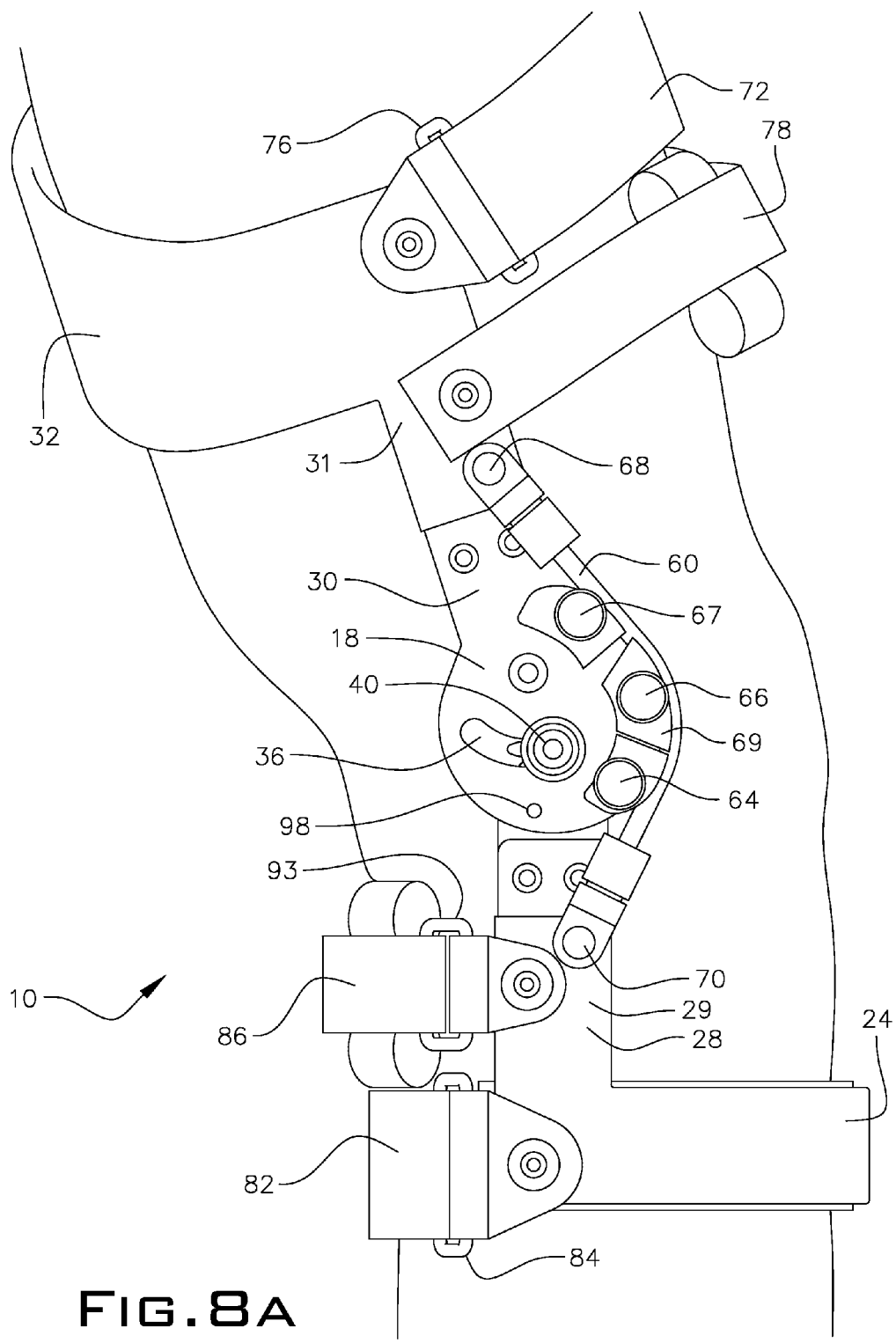
FIG. 8A is a side view of the polycentric hinge assembly with dynamic fulcrum employed with the OA knee brace of the present invention, wherein the leg of a patient is extended and with the setting blocks moved to an extreme position.
Figure 8B:
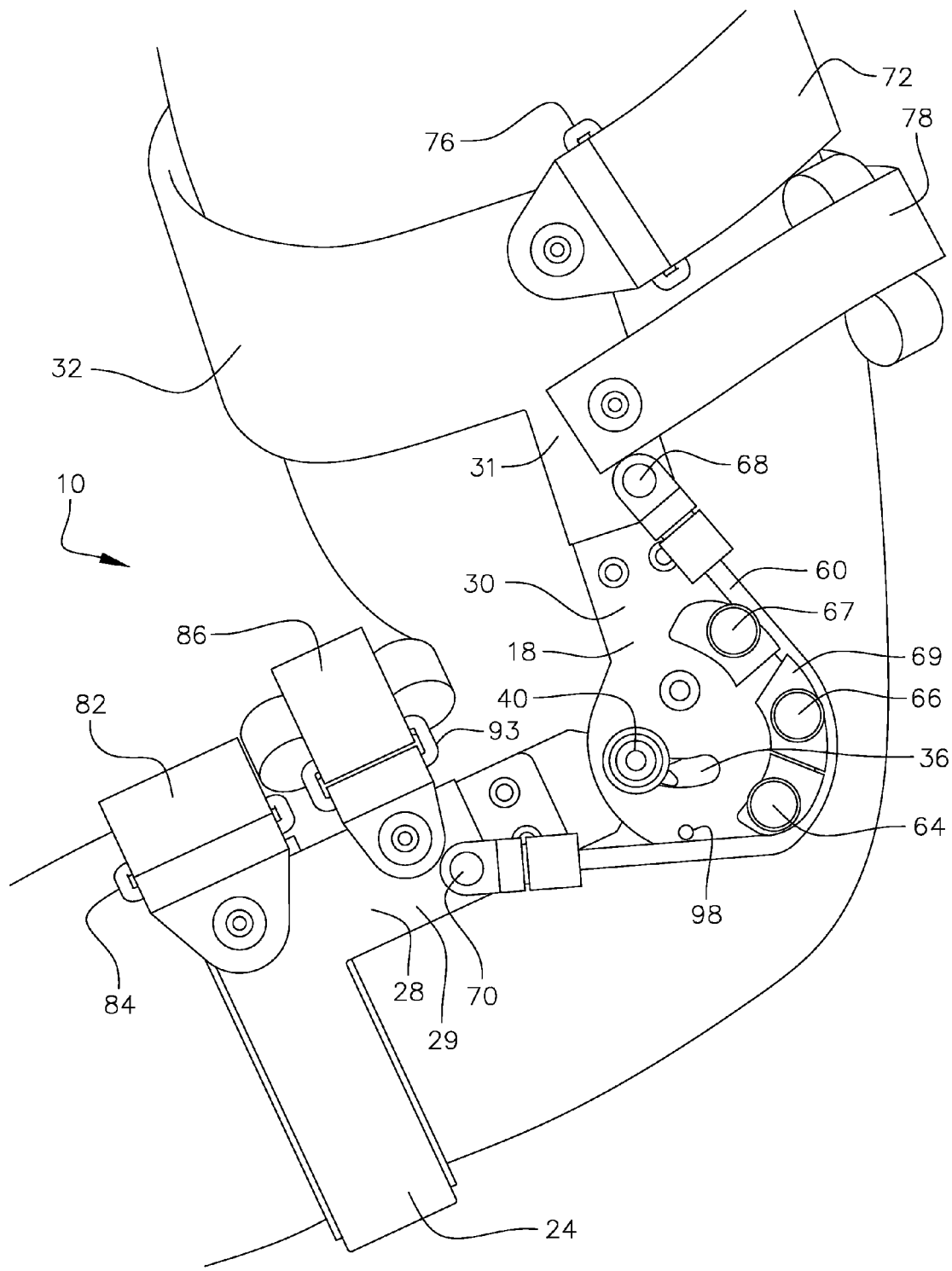
FIG. 8B is a side view according to according to FIG. 8A with the patient's knee bent.

Referring to FIGS. 5A and 5B, it is shown how adjustable dynamic fulcrum 69 is used with an alignment of three dynamic setting blocks, 62, 64 and 66, respectively. Whereas in FIGS. 6A and 6B it is shown how adjustable dynamic fulcrum 69 is aligned with only two blocks, 62 and 64, respectively. Further, FIGS. 7A and 7B show the use of adjustable dynamic fulcrum 69 with a minimal alignment wherein only one block 62 is employed. Finally, FIGS. 8A and 8B show an extreme alignment set-up wherein blocks 64, 66 and 67, respectively, are employed. In this condition, there is no block 62 in lower aperture 98 of hinge 18, but instead block 67 is positioned in upper aperture 92, of which can be seen in FIGS. 5A through 7B. It should be understood that other set-ups of block combinations not shown herein can be employed to achieve a multitude of different tension settings, which in turn can be further fine tuned and varied by using elastic band 60 of varying elasticity. Further, nothing herein requires that any two blocks be juxtaposedly positioned.

Adjustable dynamic fulcrum 69 also provides a novel swing-assist system for OA brace 10 to help the patient during gait by propelling the leg outwardly in front of them and thereby assisting the patient in their walking kinetics. The swing-assist is one of the features of the novel present invention that helps the patient to realize a more normal gait, which then translates into less hip swing and a much more realized proper heel-to-toe foot placement. Although adjustable dynamic fulcrum 69 is the preferred swing-assist system of the present invention, other like systems could be employed wherein springs are used to achieve the necessary novel swing-assist in an OA brace 10 as developed by the inventor.

Referring back to FIGS. 1 and 2, it is shown that a first anterior high-thigh cuff strap 72, made from a soft elastic material, tightens posterior upper thigh cuff 32 in place. A second anterior mid-thigh cuff strap 78, positioned slightly below strap 72, has a soft adjustable pad 74 placed at an inner midpoint area thereof and is used to provide additional securing capabilities for OA brace 10 to the patient's knee. Pad 74 eliminates potential pressure and shear on the patient's skin when wearing OA brace 10. Pad 74 attaches to stap8 by hook and loop material. Strap 72 is placed through a first D-ring fastener 76 on a first terminal side of posterior upper thigh cuff 32. Hook and loop material is used to engage strap 72 to itself. Strap 78 travels from an opposed side of OA brace 10 through a second D-ring fastener 80, opposed from first D-ring 76, and then fastens to itself by hook and loop material.

As shown in FIG. 2, a posterior shin cuff securing strap 82 travels across the back of the patient's calf through a third D-ring fastener 84 on a lower end of second lower upright member 28 and fastens onto itself with hook and loop material. A posterior padded calf strap 86, positioned slightly above strap 82 also travels around the back of the patient's calf and includes an adjustable pad 88 located at a middle portion thereof. Pad 88 also eliminates potential pressure and shear on the patient's skin when wearing OA brace 10. Pad 88 attaches to strap 86 by hook and loop material. Strap 86 passes through a fourth D-ring fastener 93 on second lower upright member 28, positioned slightly above third D-ring 84, and also attaches to itself by hook and loop material. Padded calf strap 86 is also provided with extra elastic material to provide more comfort when the patient is squatting or bending as an improvement over the prior art.

First, second, third and fourth D-ring fasteners 76, 80, 84 and 93 have all been described in preferred positions. However, nothing herein limits the movement of any of the four D-rings to one side of the brace or the other in alternate embodiments of the present invention.

OA Knee brace 10 bends by the free movement of axial hinges 12 and 18, each with a plurality of equivalently sized axial teeth (also referred to as star gears 43 and 42) on the upper and lower gear plates 44 and 26, respectively, of the inner hinge assembly of both hinges 12 and 18 (see FIG. 2 for an example of the inner hinge assembly of hinge 18). As the patient's knee bends, the bending movement is tracked or guided by rigid brace uprights (the struts), which surround each hinge 12 and 18 at upper and lower ends, and at a center axis in hinge 12 and through slot 36 on hinge 18. Hinge 18 forces a "bend line" of OA brace 10 through slot 36 that is pre-cut into hinge 18. The specific bend movement of the patient's knee is therefore controlled by a hinge axle traveling through slot 36 of hinge 18.

The adjustable dynamic fulcrum 69 on hinge 18, in this example, can be set to provide a dynamic assist mechanism between blocks 62, 64 and 66 and elastic band 60 to assist in controlling the alignment and movement of the knee from 20° of flexion to full extension of the knee. The adjustable properties of the dynamic fulcrum 69 provide the fitter or wearer of OA brace 10 a multitude of settings to maintain a comfortable knee joint space balance and an improved knee joint alignment, as well as assisting to prevent "Reverse Screw-Home Mechanism" or a controlled rotation of the knee as the knee goes from 20° flexion to extension.

Elastic band 60 and adjustable dynamic fulcrum 69 are positioned on the lateral upright strut of the OA knee brace 10 for medial compartment osteoarthritis (as shown in FIG. 4), but conversely positioned on the medial side for lateral compartment osteoarthritis (although not shown). In some patients having lateral compartment OA, the upright configuration for medial compartment OA provides the greatest benefits to unload the knee and is the preferred embodiment for upright positioning and thigh cuff angulation. Further, although not required, adjustable dynamic fulcrum 69 in the preferred embodiment is employed with polycentric hinge 18. Still further, although again not required, polycentric hinge 18 is located on the opposed side of the compacted damaged knee joint.

With reference to FIGS. 5A through 8B, four threaded holes 92, 94, 96 and 98 are arranged along hinge 18 of slotted hinge connector plate 34. Blocks 62, 64, 66 and 67 are screwed or inserted into their respective hole as needed. Block 64 is typically inserted in hole 96 for providing the center point of adjustable dynamic fulcrum 69 as the knee bends when the optimal dynamic setting of the adjustable pull mechanism of fulcrum 69 is needed. Block 62 is typically inserted into threaded hole 98 if a further optimal dynamic setting of the adjustable pull mechanism (fulcrum 69) is needed. A third adjustable dynamic fulcrum mechanism is available by inserting block 66 into threaded hole 94. In each of the aforementioned setups, elastic band 60 is tracked over the block or blocks employed thereon. By providing three or more incrementally stronger or more elastic bands, the fitter or wearer will have multiple settings to adjust dynamic fulcrum 69 to maintain a correct amount of dynamic force and to also maintain optimal joint space on both the medial and lateral compartments of the knee, as well as maintain optimal knee alignment during the motion of the knee during ambulation.

Figure 9:
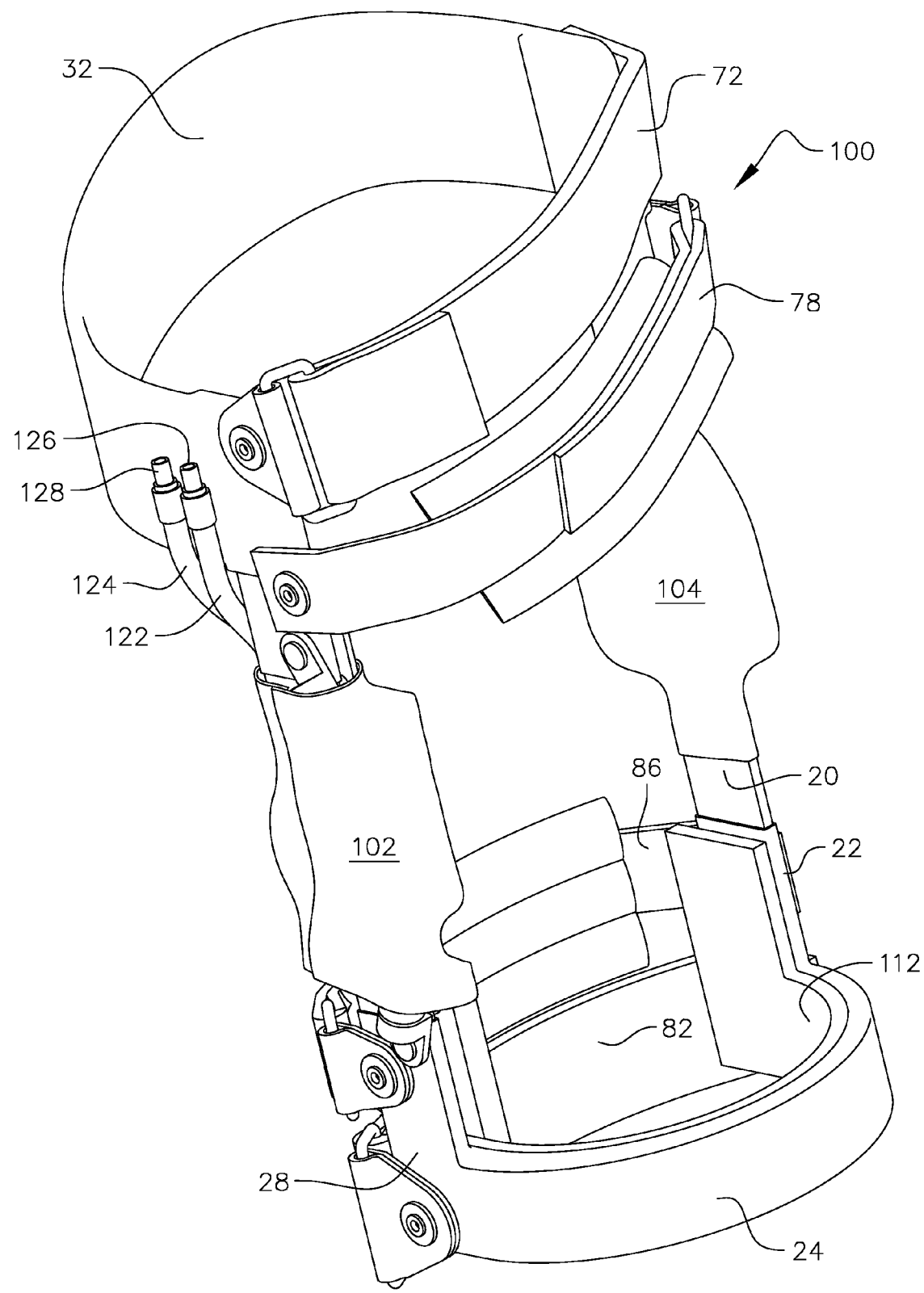
FIG. 9 is a perspective view of a preferred embodiment of an OA knee brace of the present invention wherein corrective and therapeutic force inflatable bladders are employed but covered by soft wrapping.

Referring now to FIG. 9, a preferred embodiment of the present invention is shown. In particular, OA brace 100 is shown having all of the aforementioned elements as that of OA brace 10, such as anterior shin cuff 24, angled upper thigh cuff 32, anterior high-thigh cuff strap 72, mid-thigh cuff strap 78, shin cuff securing strap 82 and calf strap 86, to name just a few. In this preferred embodiment however, a plurality of inflatable bladder systems are employed (see FIGS. 10-15) to provide varus and valgus corrective and therapeutic forces to the knee joint area and lower leg potion below the knee joint, to assist in the correction of walking gait kinetics and to provide rehabilitative action to the compartmentally damaged knee joint. The inflatable bladder systems also assist in preventing knee brace 100 from slipping when worn and to also provide a degree of advanced comfort over all prior art devices. Still further, the inflatable bladder systems also provide pressure to the leg, which assists in the overall leg straightening process and assists in the prevention of abnormal rotation of the knee. The inflatable bladder systems therefore are a means for providing a varus and valgus corrective and therapeutic force to an OA knee joint.

As shown in FIG. 9, both polycentric hinge 18 and uni-centric hinge 12 are covered by a pair of soft and pliable wraps 102 and 104, respectively, and are used when OA brace 100 is employed to the patient's knee. The inner surfaces of pliable wraps 102 and 104 employ a material having a high coefficient of friction which assists in a more comfortable fit for the wearer and reduces or eliminates brace slippage. Further this unique material actually works better when moisture is introduced thereto, which is a very common occurrence through sweating by the patient.

Figure 10:
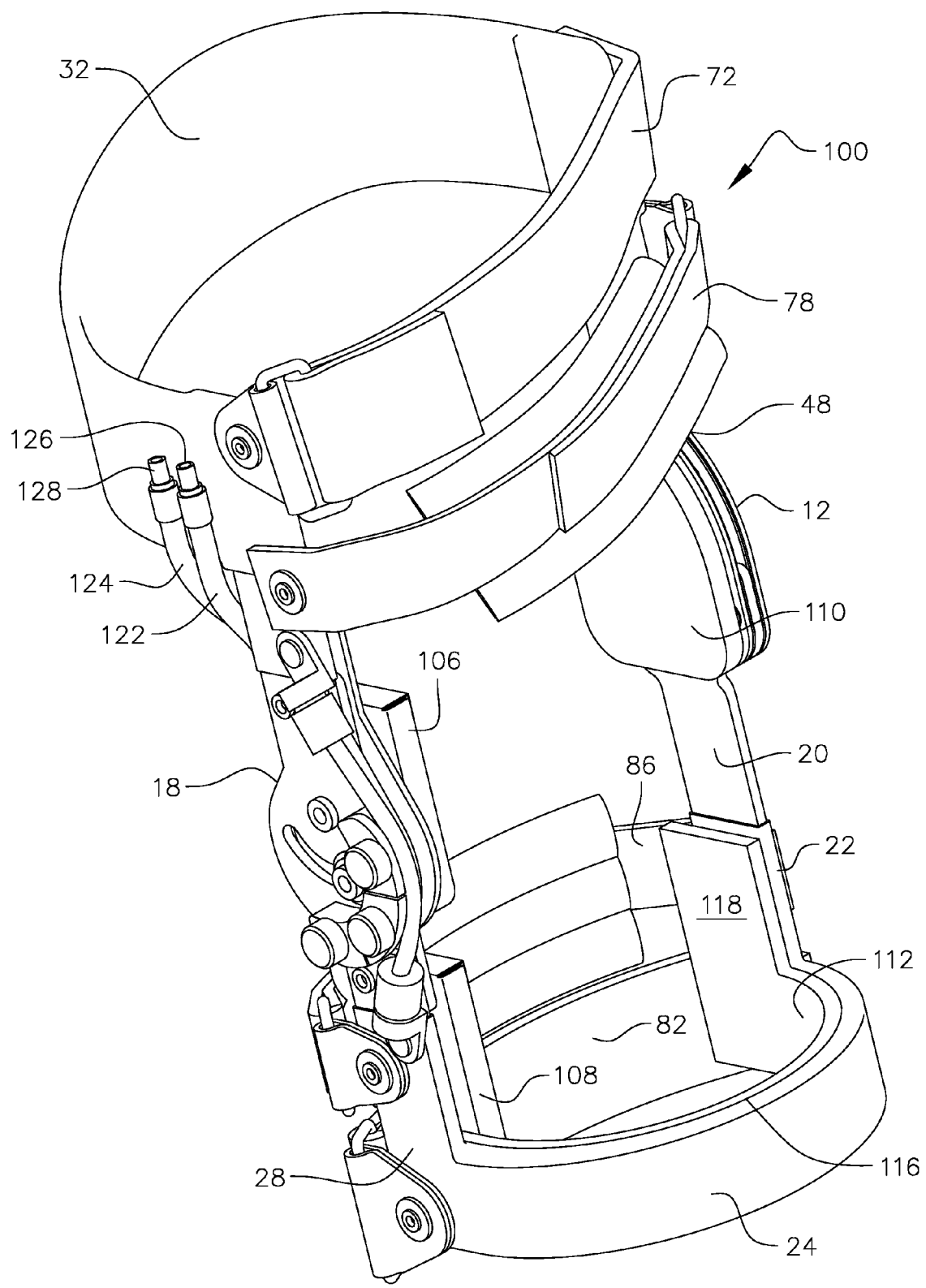
FIG. 10 is a perspective view of the preferred embodiment of the OA knee brace of the present invention illustrating the corrective and therapeutic force inflatable bladders "unwrapped;"
Figure 11:
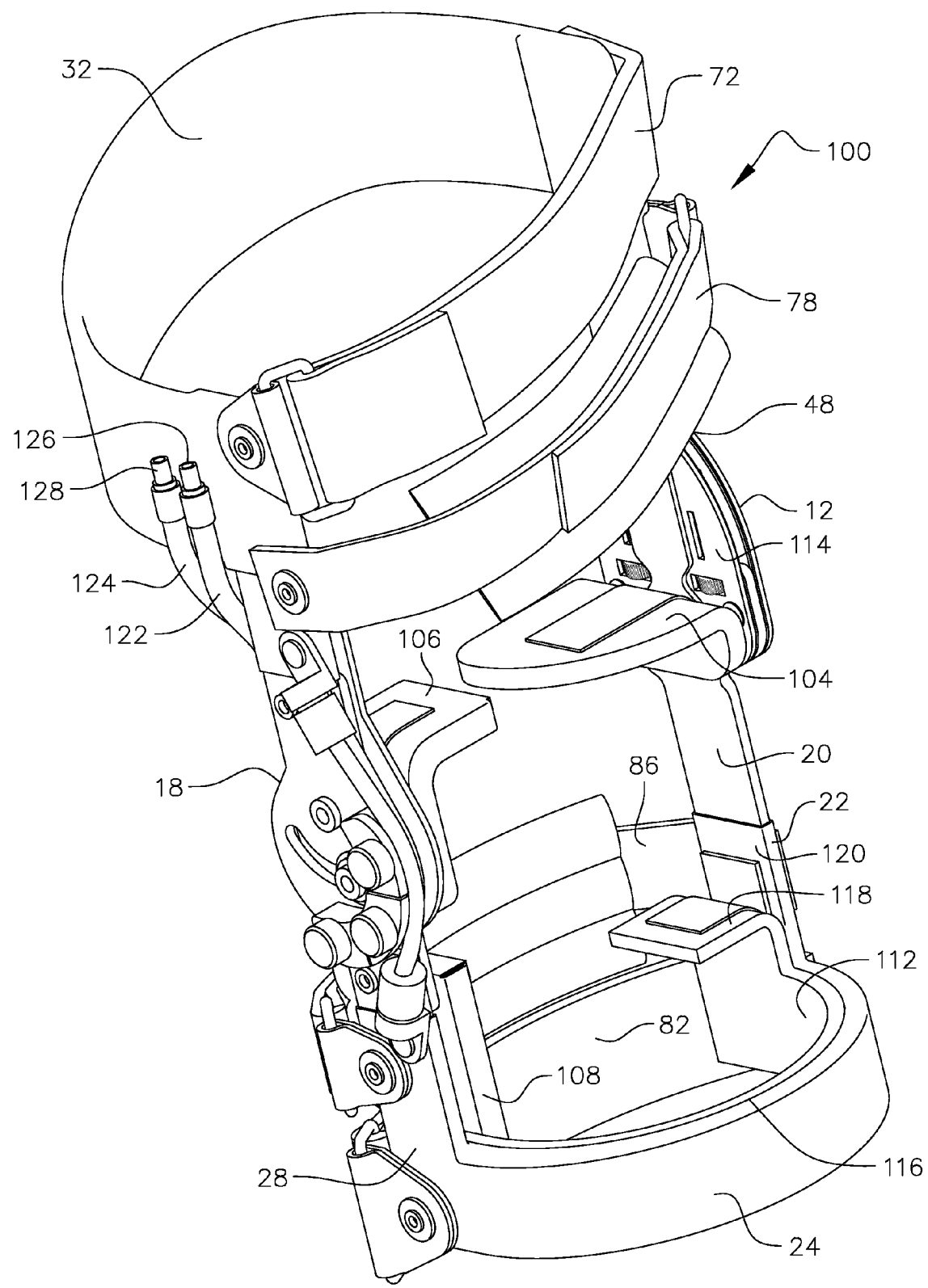
FIG. 11 is a perspective view of the preferred embodiment of the OA knee brace of the present invention illustrating how the corrective and therapeutic force inflatable bladders and other cushion pads, attached to said knee brace, can be detached and repositioned to specifically place the corrective and therapeutic force system where it is needed.

As shown in FIG. 10, the plurality of inflatable air bladder systems includes at least an upper bladder system 106 and a lower bladder system 108. However, more than two bladder systems can be employed if desired, such as an embodiment employing three or four bladder systems. OA brace 100 also includes upper cushion pad 110 and an L-shaped inner shin cuff cushion pad 112 having the same curved shape as shin cuff 24. Referring to FIG. 11, it is shown that upper bladder system 106, lower bladder system 108, upper cushion pad 110 and L-shaped inner shin cuff cushion pad 112 are all removable (or detachable) for re-positioning in a multitude of various set-ups that are illustrated in FIGS. 12-15. Each of these four elements, 106, 108, 110 and 112 are all attached to OA brace 100 by means of hook and loop material, although other attachment means can be employed.

Figure 12:
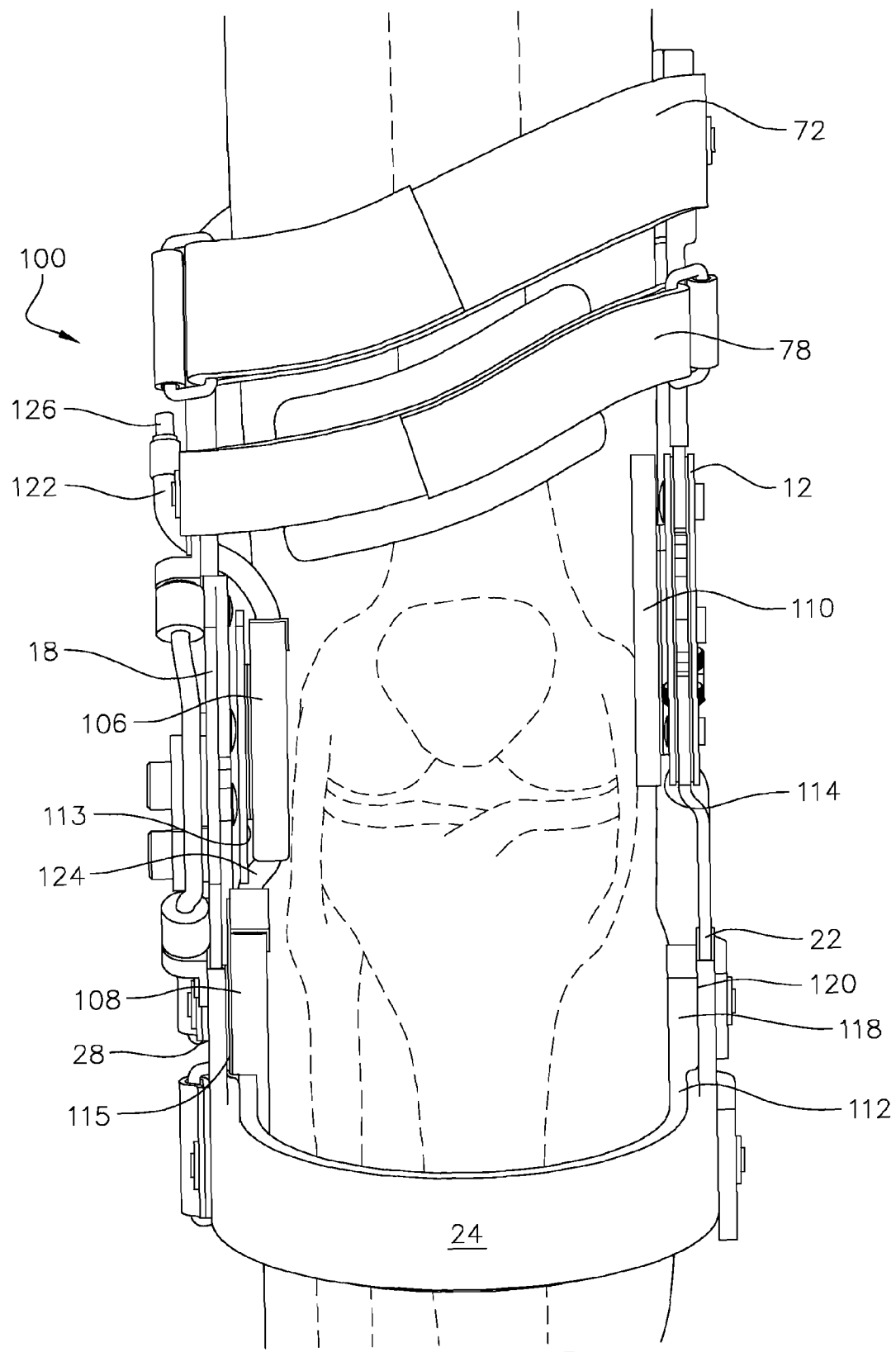
FIG. 12 is a front view of a medial compartmentally damaged knee wherein the hidden view illustrates said knee being "unloaded" by a preferred embodiment of the OA knee brace of the present invention such that upper and lower corrective and therapeutic force inflatable bladders are located on the lateral side of the knee joint.

Referring back to the embodiment of FIG. 10 which is also illustrated in FIG. 12, upper bladder system 106 is attached along an inner surface 113 (see FIG. 12) of polycentric hinge 18. It should be noted that inner surface 113 is that of a thin plate member that covers the gear mechanism (seen in FIG. 2) of hinge 18. Lower bladder system 108 attaches to the same side of OA brace 100 as that of upper bladder system 106, but below polycentric hinge 18, along an inner surface 115 of second lower upright member 28. Upper cushion pad 110 is affixed to an inner surface 114 (see FIG. 11) of uni-centric hinge 12. L-shaped inner shin cuff cushion pad 112 affixes along an inner surface 116 of shin cuff 24 and has an upright portion 118 that attaches to an inner surface 120 (see FIG. 11) of first lower upright member 22.

As shown in FIGS. 10-15, a plurality of different bladder system set-ups are shown, which illustrate the varying locations that the upper and lower bladder systems, 106 and 108 respectively, can be positioned in the present invention. It is understood that FIGS. 10-15 do not show every possible bladder system set-up. However, none of the plurality of different bladder system set-ups includes positioning bladders 106 and 108 above the knee joint and above hinges 12 and 18 on upper arms 48 and 30 (see FIG. 4). Further, all bladder system set-ups are only positionable along inner surfaces 113, 114, 115 and 120, which are all located at or below the knee joint and never above the hinges.

Although not shown, the upper and lower bladder can actually be a single bladder separated by a small channel, which permits the placement of the corrective and therapeutic forces at the same or more places along the knee joint area and lower leg (such as when more than two compartments are employed on the bladder system, with each compartment being separated by an air channel). Further, although not shown, the bladder systems can actually be embedded within the vertical struts and allow for a custom designed OA brace of the present invention to be built for each patient in need thereof.

Referring to FIGS. 9-11, it is shown that upper and lower bladder systems, 106 and 108, each have an inflation tube, 122 and 124 respectively, which in turn each have a nozzle 126 and 128, respectively, which are used to both inflate and deflate bladder systems 106 and 108. A different colored nozzle, such as black and white, can be used to distinguish the two inflation tubes when juxtaposedly positioned close to one another as in the embodiment of FIGS. 9-11.

Figure 16:
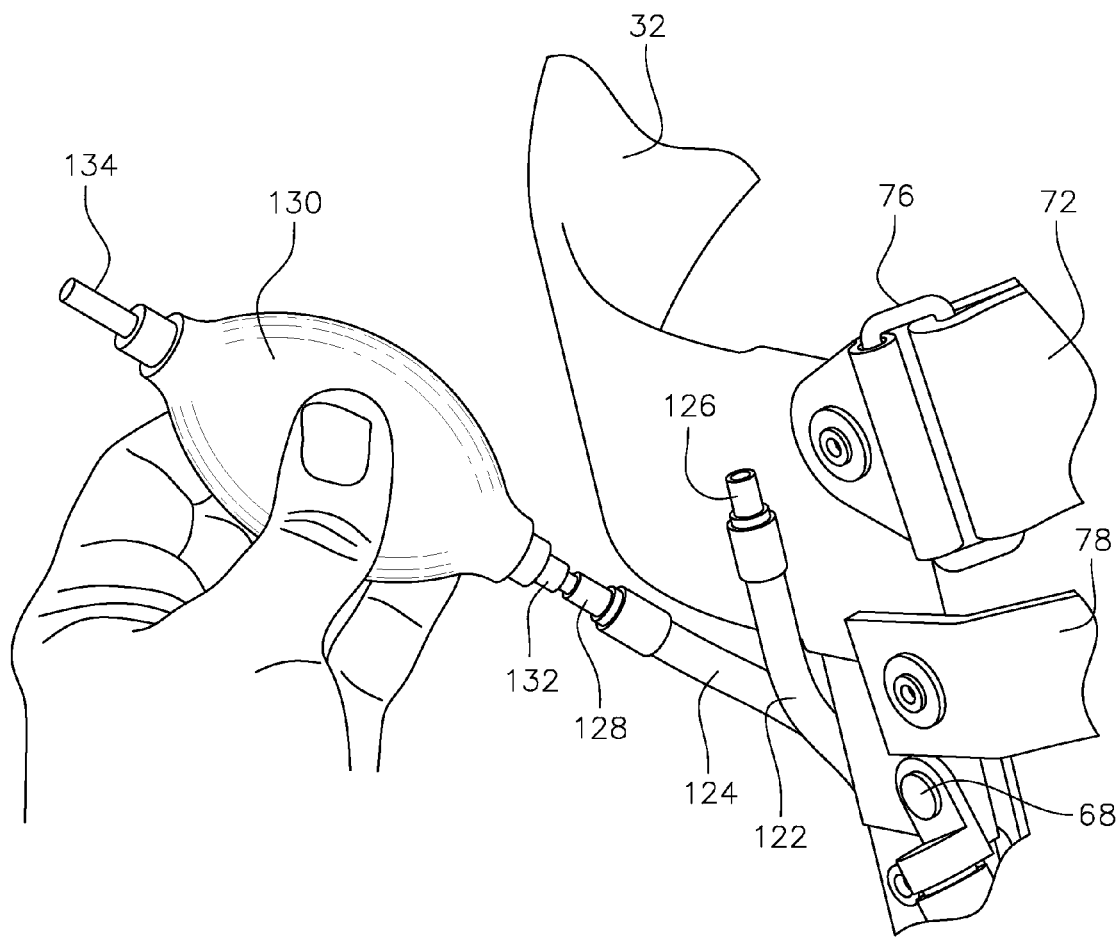
FIG. 16 is a perspective view in partial of the OA knee brace of the present invention illustrating how the inflatable bladders are inflated and deflated.

Referring now to FIG. 16, it is shown how bladder systems 106 and 108 are inflated or deflated. In particular, a bulbous hand pump 130 is employed having opposed end tips 132 and 134. Tip 132 inserts into nozzle 126 or 128 to inflate the bladder systems, whereas tip 134 inserts into nozzle 126 or 128 to deflate the bladder systems. Accordingly, as shown in FIG. 16, when a person squeezes pump 130, tip 132 will push air out for inflating a bladder system whereas tip 134 will draw or suck air in for deflating a bladder system, when attached a nozzle 126 or 128.

Figure 17:
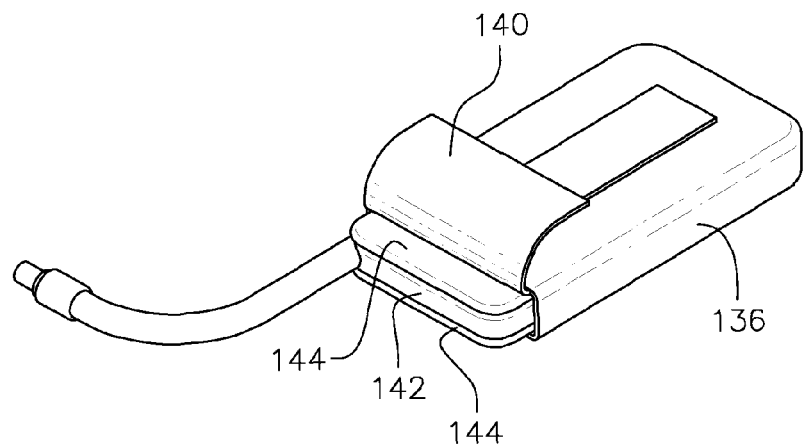
FIG. 17 is a perspective view of a bladder packet employed in the OA knee brace of the present invention.
Figure 18:
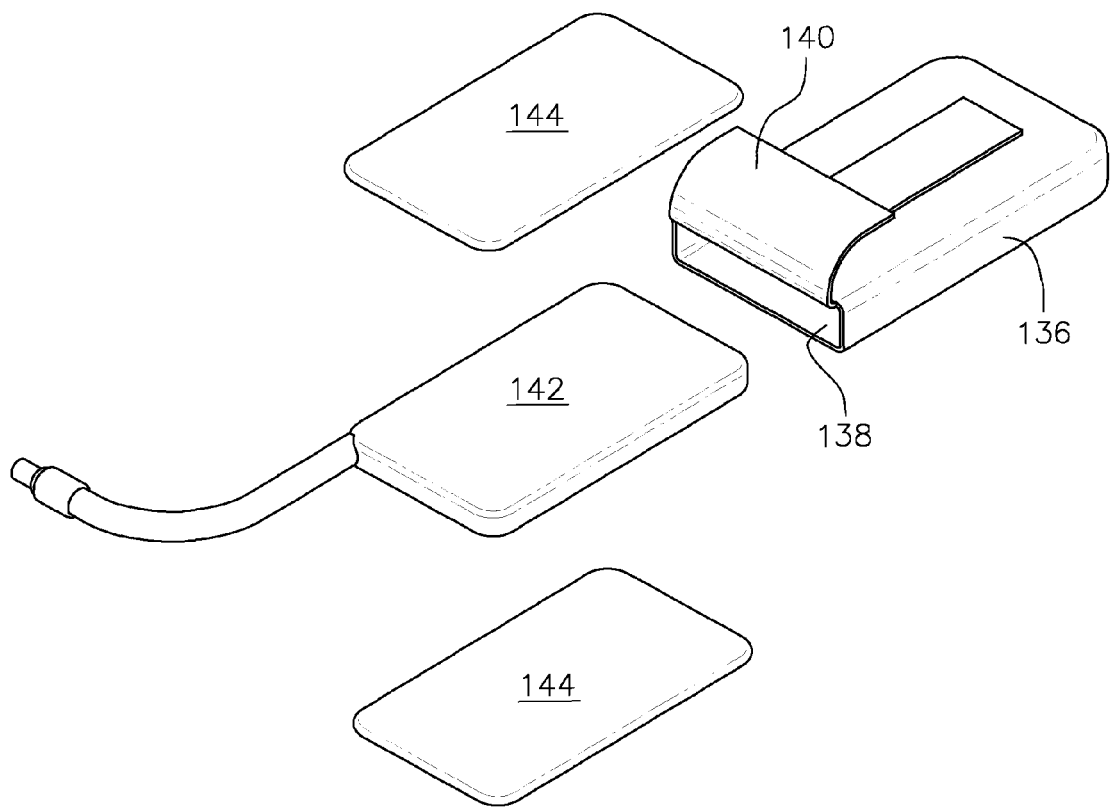
FIG. 18 is an exploded view of FIG. 17.

With reference to FIGS. 17 and 18, it is shown that the bladder system used in the present invention include a soft and pliable retaining pouch 136 having a pocket 138, closable by a cover flap 140, which uses hook and loop material to secure cover flap 140 to pouch 136. Further, a bladder member 142 of soft neoprene or other like material is employed and can then be surrounded by a pair of insert units 144, which can be planar, generally planar, concave, convex or anatomically shaped, and which can be employed within pocket 138 in any combination of these varying shapes. A preferred embodiment employs just one insert unit 144, which is located in pouch 136 on the side of the bladder system that comes in contact with the patient's knee area. In yet another alternate embodiment, no insert units 144 are employed with the bladder systems. Further, pliable retaining pouch 136 can include piece of material or can be made entirely from a material having a high coefficient of friction. This again helps to prevent brace slippage when worn and to reduce or eliminate skin irritation, which is a well known, but unsolved problem in the prior art. The use of the material having a high coefficient of friction in the present invention on various elements of the novel OA brace 100 reduces overall brace slippage and provides an enhance comfort for the patient when brace 100 is employed. In the preferred embodiment, a cami-suede is used. However, other like materials, having similar properties, can be employed to achieve the same result as described directly hereinabove.

With further reference to FIGS. 17 and 18, insert units 144 are made from shaped rigid or semi-rigid material, such as a pliable plastic. Regardless if one or more insert unit is employed the one that comes in contact with the knee joint area, and therefore has the inflatable bladder positioned there behind, contours and thereby equally distributes the desired corrective and therapeutic force that each bladder system exerts against the area of respective contact. The distribution of force can therefore be equalized and controlled across the entire surface of the knee joint area to prevent or minimize unwarranted pressure at any given point of contact and provide a level of comfort never before realized in an OA knee brace until now. Still further, a layer of foam can be employed along insert 144 for added comfort and can also include a very small overlapped portion that covers the peripheral edge of insert 144 to avoid unwanted "pinching" by said insert.

As further shown in FIGS. 17 and 18, insert unit 144 and bladder member 142 have longitudinal axes that are in parallel with one another when inserted within pliable retaining pouch 136 and which form bladder systems 106 and 108. Further, insert unit 144 is never employed outside of pliable retaining pouch 136 wherein bladder member 142 is located, but instead always inside thereof with bladder member 142, as shown in FIG. 17.

Other corrective and therapeutic force inflatable bladder systems having controlled bladder shaping mechanisms, such as insert units 144 described herein, can be employed with the corrective and therapeutic force system of the present invention to achieve the same result. Still further insert units 144 can be fabricated from an anatomically formable material, like that seen with diabetic insole orthotics, wherein a group of polymers are employed, which can be chosen from the group, but not limited to, polyurethane (PUR), ethylene vinyl acetate (EVA), polyethylene (PE), polyvinylchloride (PVC) and vulcanized rubber.

Figure 13:
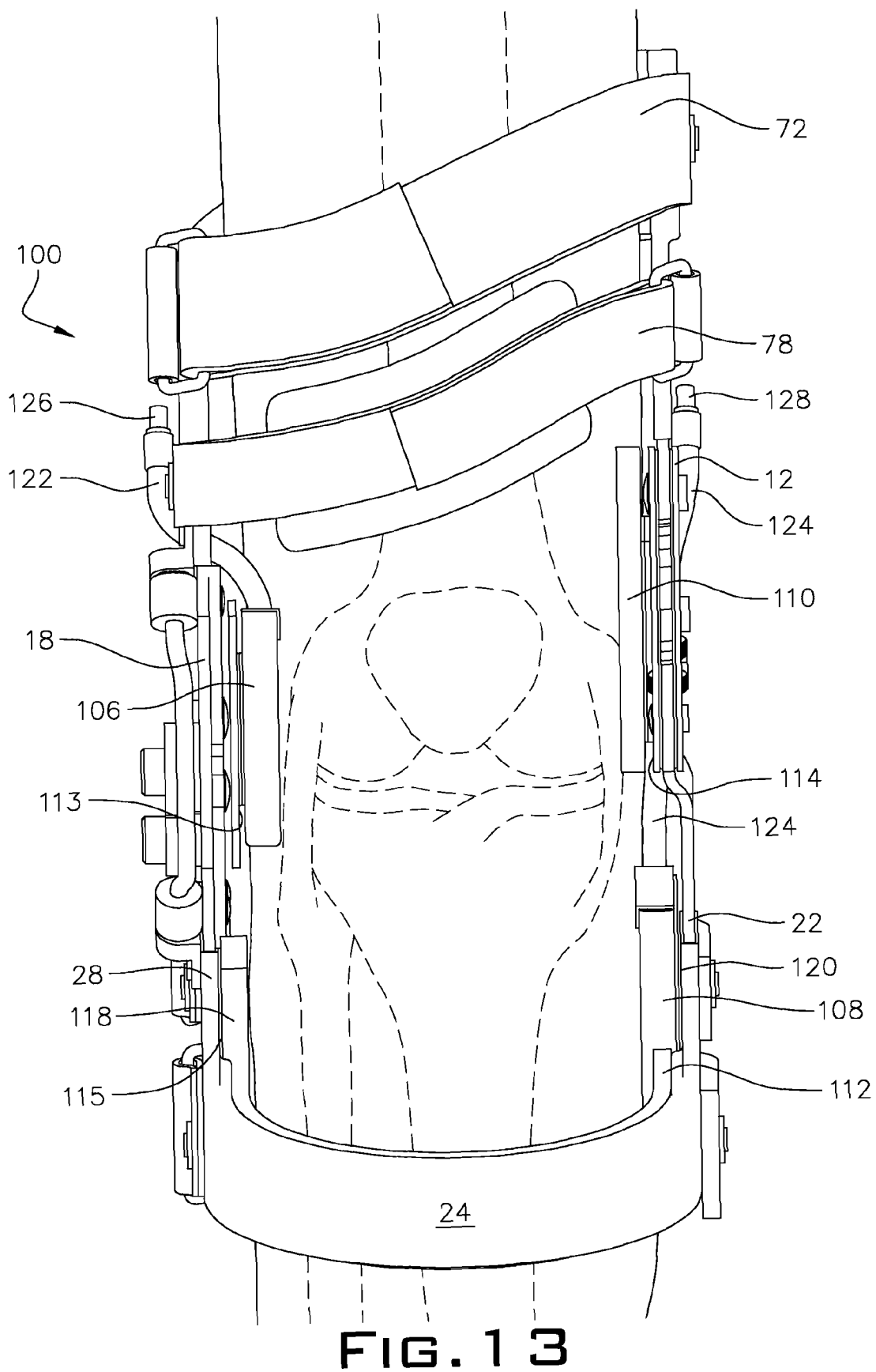
FIG. 13 is a front view of a medial compartmentally damaged knee wherein the hidden view illustrates said knee being "unloaded" by a first alternate preferred embodiment of the OA knee brace of the present invention, wherein an upper corrective and therapeutic force inflatable bladder is located on the lateral side and a lower corrective and therapeutic force inflatable bladder is located on the medial side of the knee joint.

Referring to FIG. 13, a first alternate preferred embodiment is shown wherein preferred OA brace 100 employs upper bladder system 106 along inner surface 113 of hinge 18 and lower bladder system 108 on the opposed side of brace 100 along inner surface 120 of first lower upright member 22, below hinge 12. Therefore, upper and lower bladder system inflation tubes, 122 and 124 respectively, are disposed on opposite sides of brace 100, as shown therein. In this embodiment, upper cushion pad 110 remains attached to inner surface 114 of hinge 12. Also, L-shaped cushion pad 112 is reversed as compared to the embodiment shown in FIG. 12 such that upright portion 118 of cushion pad 112 attaches to inner surface 115 of second lower upright member 28.

Figure 14:
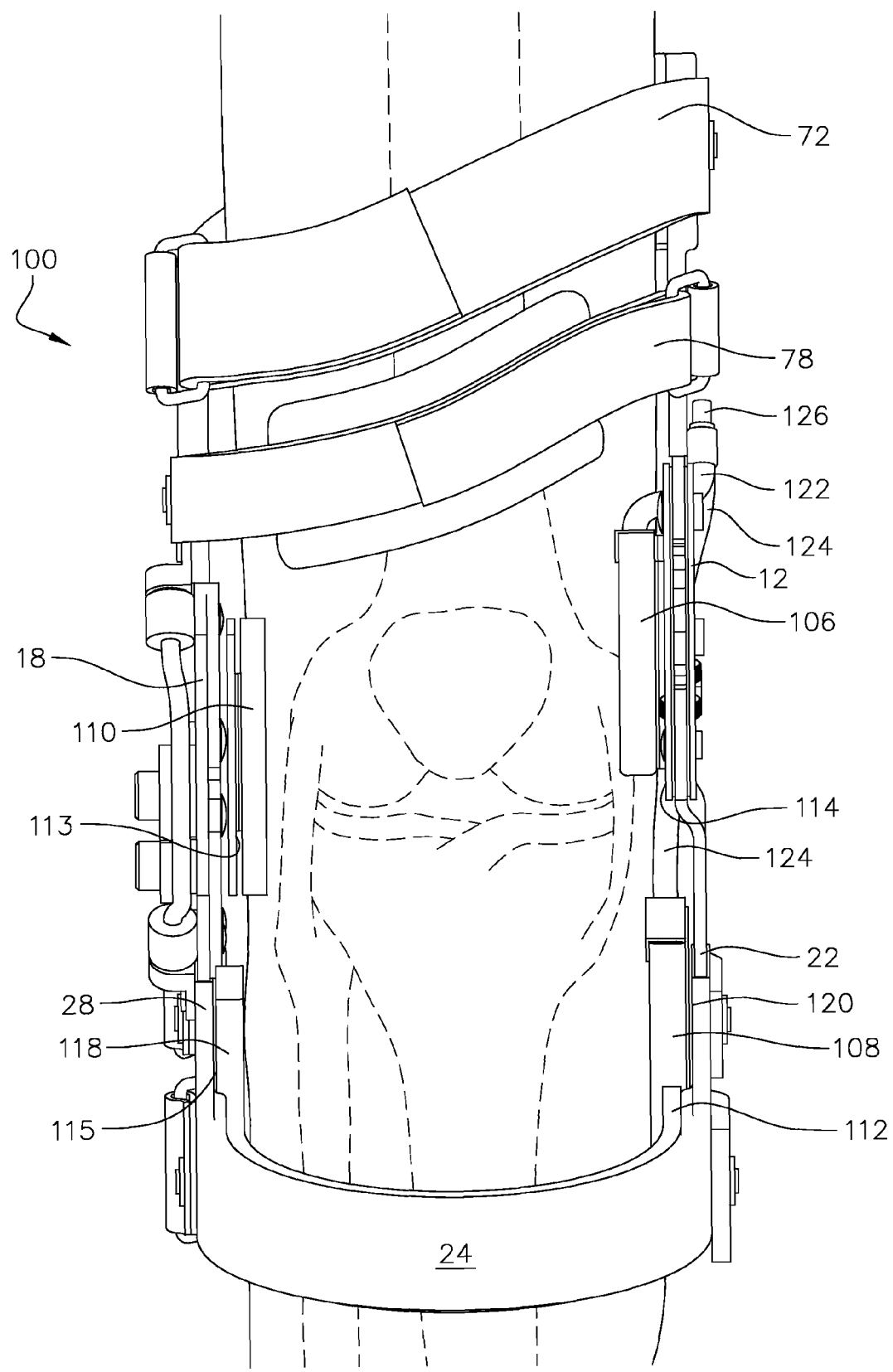
FIG. 14 is a front view of a medial compartmentally damaged knee wherein the hidden view illustrates said knee being "unloaded" by a second alternate preferred embodiment of the OA knee brace of the present invention, wherein both the upper and lower corrective and therapeutic force inflatable bladders are located on the medial side of the knee joint.

Referring now to FIG. 14, a second alternate preferred embodiment is shown wherein preferred OA brace 100 employs upper bladder system 106 along inner surface 114 of hinge 12 and lower bladder system 108 on the same side of brace 100 along inner surface 120 of first lower upright member 22, below hinge 12. Therefore, upper and lower bladder system inflation tubes, 122 and 124 respectively, are disposed on the same side of brace 100, as shown therein. In this embodiment, upper cushion pad 110 attaches to inner surface 113 of hinge 18. Also, L-shaped cushion pad 112 is reversed as compared to the embodiment shown in FIG. 12, but the same as compared to the embodiment of FIG. 13 wherein upright portion 118 of cushion pad 112 attaches to inner surface 115 of second lower upright member 28.

Figure 15:
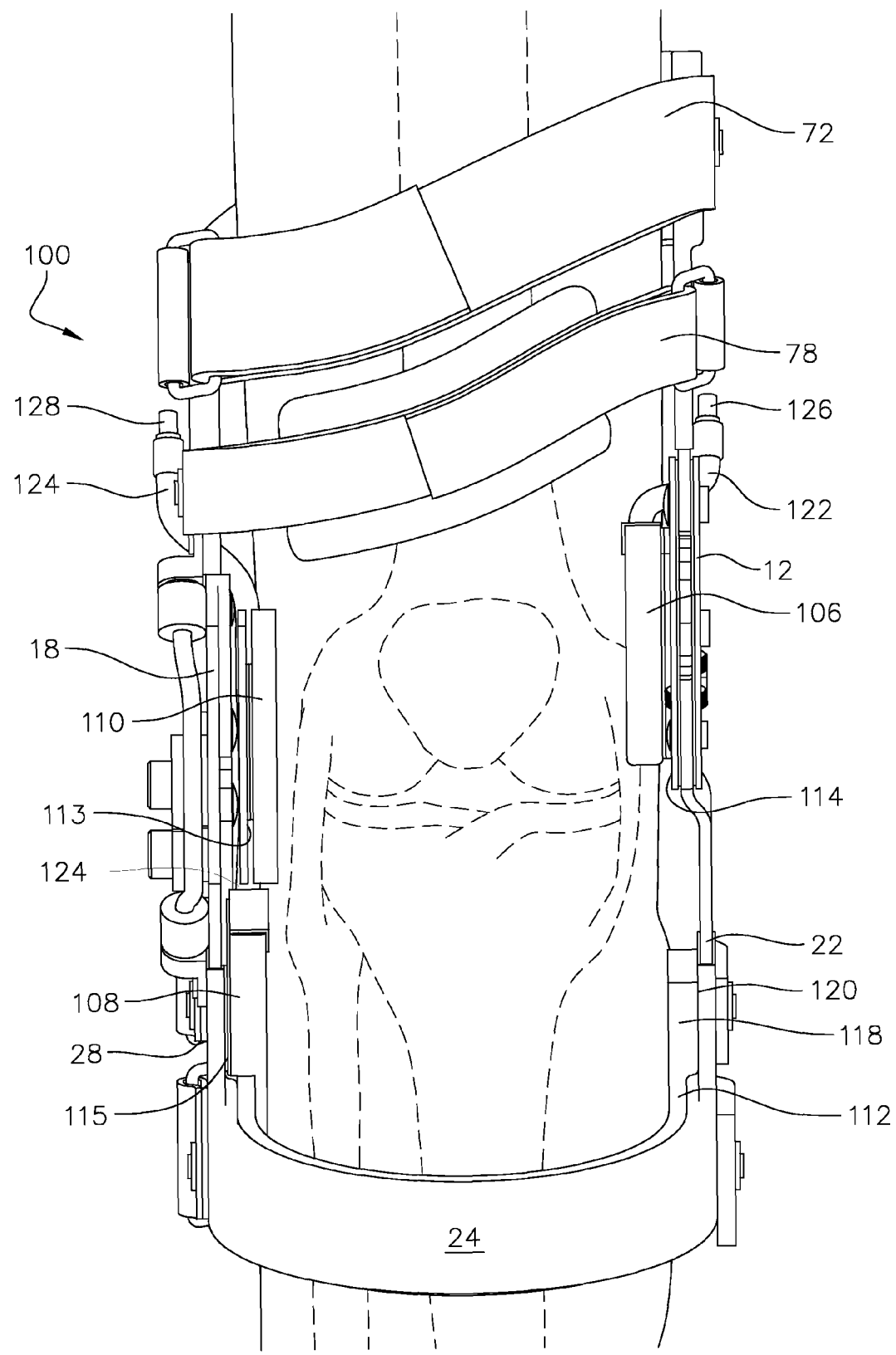
FIG. 15 is a front view of a medial compartmentally damaged knee wherein the hidden view illustrates said knee being "unloaded" by a third alternate preferred embodiment of the OA knee brace of the present invention, wherein an upper corrective and therapeutic force inflatable bladder is located on the medial side and a lower corrective and therapeutic force inflatable bladder is located on the lateral side of the knee joint.

With reference now to FIG. 15, a third alternate preferred embodiment is shown wherein preferred OA brace 100 employs upper bladder system 106 along inner surface 114 of hinge 12 and lower bladder system 108 on the opposed side of brace 100 along inner surface 115 of second lower upright member 28, below hinge 18. Therefore, upper and lower bladder system inflation tubes, 122 and 124 respectively, are disposed on opposite sides of brace 100, as shown therein. In this embodiment, upper cushion pad 110 attaches to inner surface 113 of hinge 18. However, L-shaped cushion pad 112 is reversed as compared to the first and second alternate embodiments shown in FIGS. 13 and 14, but the same as compared to the preferred embodiment of FIG. 12, wherein upright portion 118 of cushion pad 112 attaches to inner surface 118 of first lower upright member 22.

As shown in FIGS. 12 through 15, a pair of bladder systems is employed. However, although not shown, more than two bladder systems could be employed. For example, four bladder systems could be employed along inner surface 113 of hinge 18, inner surface 115 of second lower upright member 28, inner surface 114 of hinge 12 and inner surface 120 of first lower upright member 22. In such an embodiment, L-shaped cushion pad 112 is modified to not include upright portion 118, or L-shaped cushion pad could be excluded altogether. Further, three bladder systems could be employed whereby two upper bladders are attached along the inner surfaces of hinges 12 and 18 and then one lower bladder is employed on one of two sides below either hinge 12 or hinge 18. Or again, three bladder systems could be employed but with two lower bladders attached along the inner surfaces of first and second lower upright members 22 and 28 then one upper bladder is employed on one of two hinges 12 or 18. An even further alternate embodiment employs a plurality of bladders, such as six bladders, wherein two bladders are positioned at hinges 12 and 18, two more at hinges 12 and 18, and then two more above hinges 12 and 18.

Still further, nothing herein requires that a double strut design, as shown in FIGS. 12 through 15, be employed with the novel corrective and therapeutic force bladder system. Therefore, a single upright strut design can be used to accomplish the necessary varus and/or valgus correction in a patient with osteoarthritis with the novel OA brace of the present invention.

It is further understood that nothing herein requires that the corrective and therapeutic force system be only inflatable air bladders. For instance, liquid filled or pneumatic bladders using a gas other than air could be employed. Or, custom gel forms or foam pads could be made patient-specific and then employed on OA brace 100 in place of the preferred inflatable air bladders as described above.

Figure 19:
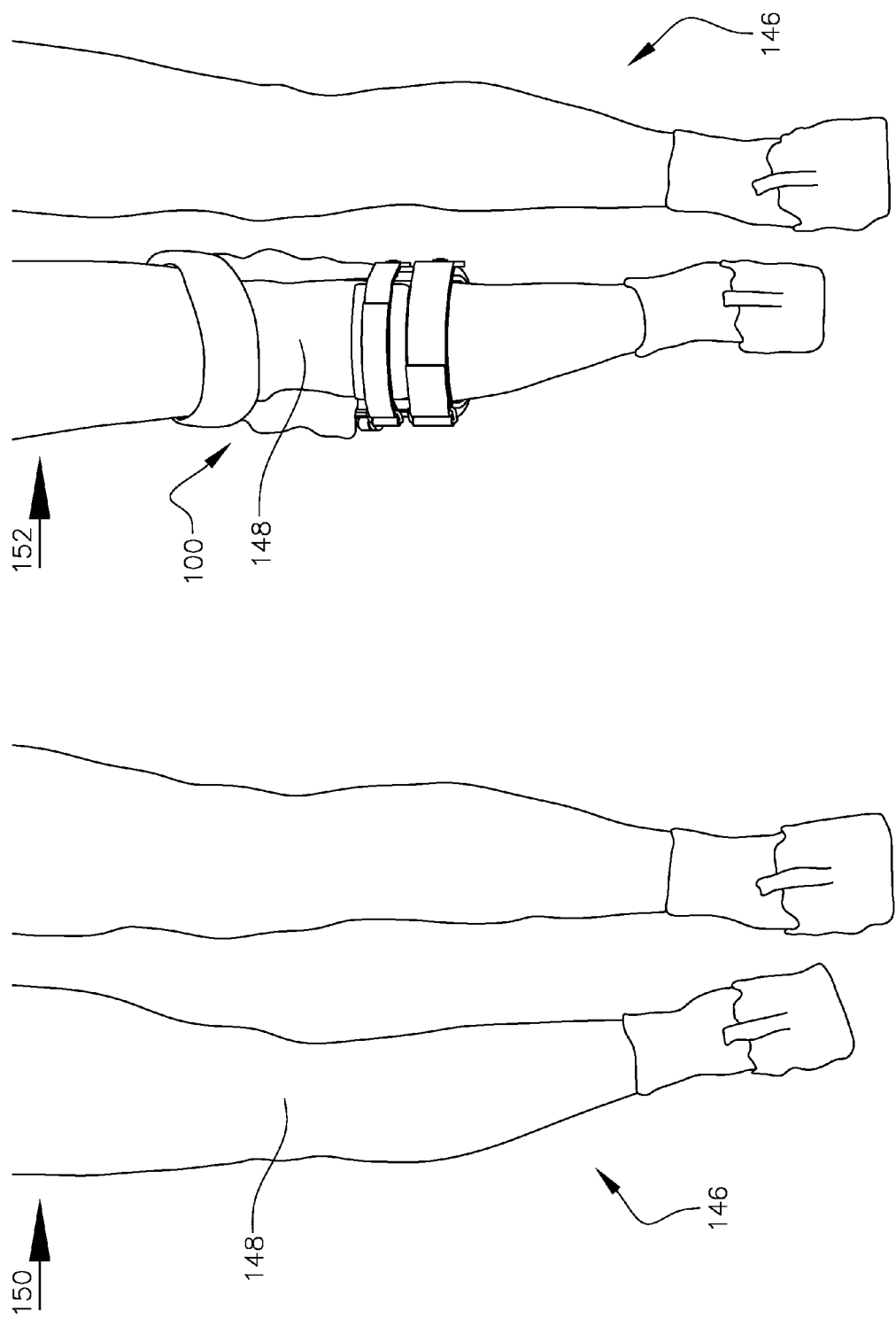
FIG. 19 is a rear view of a pair of legs of a person having medial compartmental damage of the left knee joint illustrating hip abduction of the left hip as compared to when the OA brace of the present invention is employed.
Figure 20:
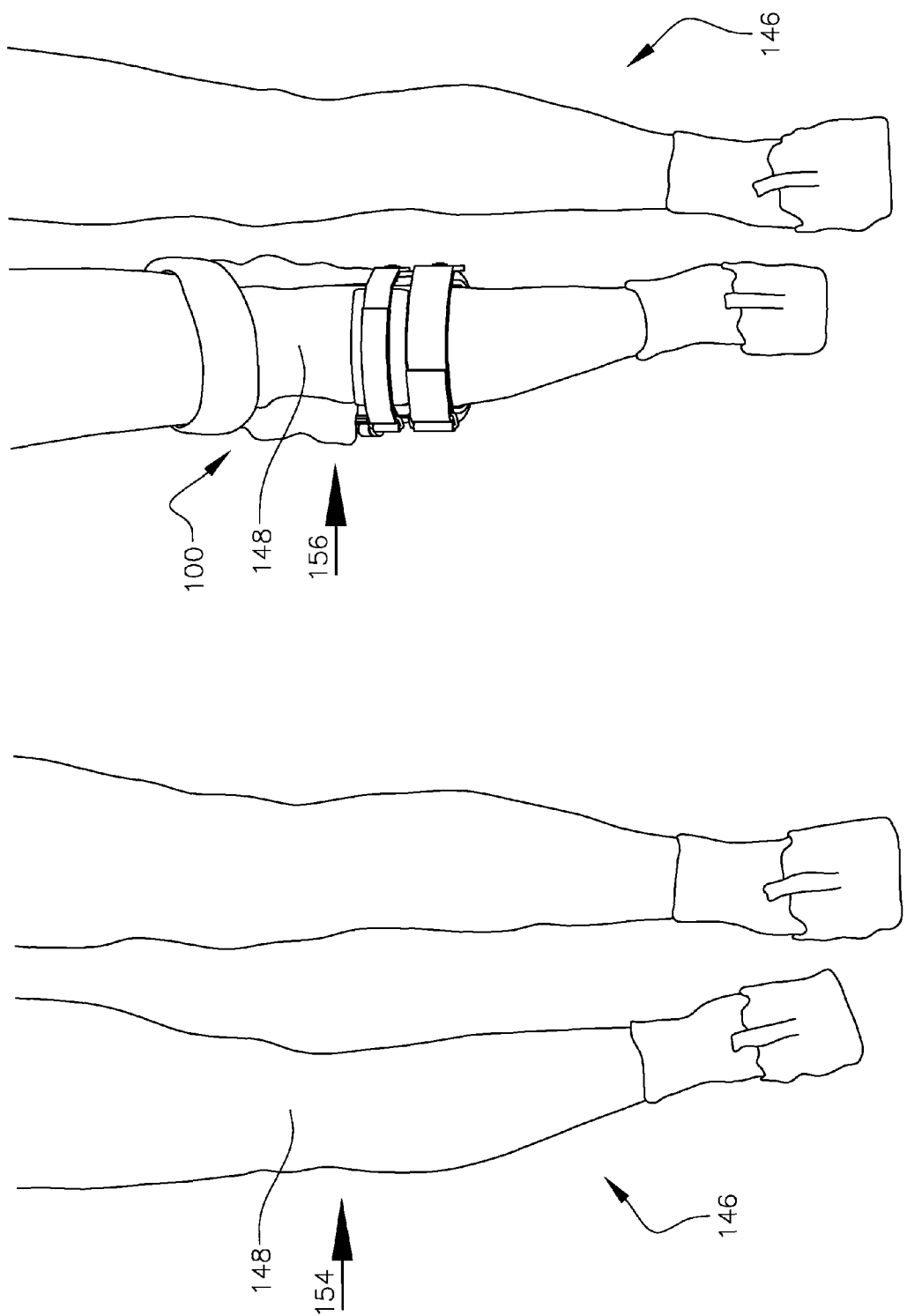
FIG. 20 is a rear view of a pair of legs of a person having medial compartmental damage of the left knee joint illustrating varus knee deformity as compared to when the OA brace of the present invention is employed.
Figure 21:
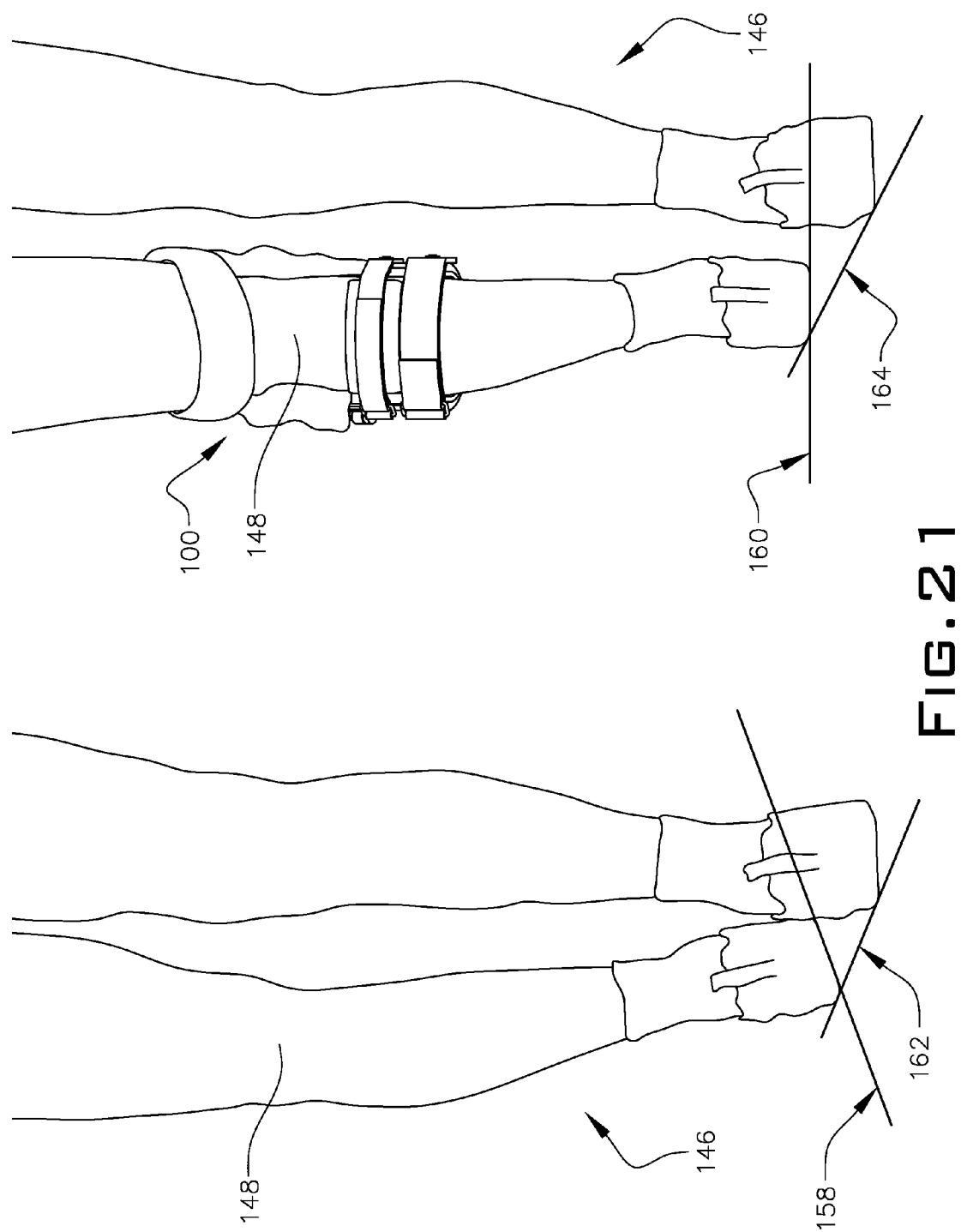
FIG. 21 is a rear view of pair of legs of a person having medial compartmental damage of the left knee joint illustrating both a reduced step length during gait as well as an abnormal lateral foot placement of the left foot as compared to when the OA brace of the present invention is employed.

With reference now to FIGS. 19-21, a pair of legs 146 having medial compartmental damage of the left knee 148 is shown on the left side of each figure with the same pair of legs 146 having the preferred OA knee brace 100 employed on said left knee 148. With specific reference to FIG. 19, arrow 150 shows significant abduction of the left hip area due to the medial compartmental damaged left knee joint. "Abduction," in functional anatomy, is a movement, which draws a body limb, or in this case, the hip, away from the median (or "Sagittal") plane of the body. This contrasts with "adduction," which is a movement that brings a limb closer to the median or "Sagittal" plane of the body. Hip abduction primarily occurs due to the patient swinging their hip outward to alleviate or to limit the pain felt in the OA damaged knee joint. However, as shown by arrow 152, the hip abduction is eliminated, or significantly curtailed, by the use of OA knee brace 100 due to a correction to a more normal gait.

With specific reference now to FIG. 20, arrow 154 shows the varus knee deformity caused by the medial compartmental damaged left knee joint, whereas arrow 156 shows a significant reduction in varus alignment when the OA brace 100 is used. In orthopedic medicine, a "varus deformity" is used to describe the inward angulation of the distal segment of a bone or joint. Therefore, in the case of a varus deformity of the knee, the distal part of the leg below the knee is deviated inward, resulting in a bowlegged appearance. Conversely, a valgus deformity of the knee results in a knock-kneed appearance, with the distal part of the leg deviated outward. FIGS. 19-21 are illustrating a varus deformity of the knee.

With reference to FIG. 21, line 158 illustrates the abnormal lateral foot placement due to the medial compartmentally damaged left knee joint as compared to the near normal heel-to-toe foot placement illustrated by line 160 when using brace 100 on said damaged knee. Finally, also in FIG. 21, line 162 illustrates the reduced step length of a patient with a medial compartmentally damaged left knee joint as compared to a more normal gait and a longer step length of line 164 when using brace 100 on said damaged knee, when comparing a point along the outer back edge of the left foot to a point along the inner back edge of the right foot.

It should also be noted, that although the preferred embodiment of the present invention shows an offset thigh cuff 32, nothing herein requires that a double upright design, as shown in FIGS. 12 through 15, be employed with the novel corrective double upright struts. Therefore, double upright struts of equal length on each side, with or without a posteriorly offset upper upright, could be employed and without an angled thigh cuff. Still further, a double upright design with uprights of equal length with a level perpendicular thigh cuff, without a posteriorly offset upright on either side, and utilizing upper bladders on each hinge and bladders on both lower uprights can be used as a universal (left or right, varus or valgus correction knee brace to unload, align, and protect the knee joint, as well as to prevent any abnormal rotation of the knee, especially after OA surgery.

It should also be understood from the description herein above that there are multiple embodiments of the present invention that can reduce, prevent or eliminate the abnormal rotation of the knee joint, which as previously stated, if left unchecked, can lead to a pathological OA condition. The specific embodiments for this include: (1) the double vertical upright, thigh cuff double off-set design (with or without the air bladder system); (2) the double vertical upright equal length strut design having no thigh cuff offset but employing the air bladder system; (3) the double vertical upright differential length strut design having no thigh cuff offset but employing the air bladder system; and (4) the single vertical upright strut design employing the air bladder system.

Other equivalent elements can be substituted for the elements disclosed herein to achieve the same results in the same way and in the same manner.

Having thus described the invention, what is claimed for Letters Patent follows:

1. An improved osteoarthritis knee brace for treating a knee joint of a patient suffering from osteoarthritis of the knee, the improved osteoarthritis knee brace comprising,
   a) at least one vertical strut having an upper and lower portion;
   b) at least one pivoting hinge intermediately disposed between the at least one vertical strut upper and lower portions;
   c) a shin cuff attached to the at least one vertical strut lower portion and positioned below at least one pivoting hinge;
   d) a thigh cuff attached to the at least vertical strut upper portion and positioned above the at least one pivoting hinge;
   e) means for applying a corrective and therapeutic force to the osteoarthritis damaged knee joint and a lower leg portion located below the knee joint, said means removeably positionable about the osteoarthritis knee brace at the knee joint and the lower leg portion along an inner surface of the at least one vertical strut lower portion and an inner surface of the at least one pivoting hinge such that the means for applying a corrective and therapeutic force makes direct contact with a side portion of the lower leg and the knee joint; and
   f) means for equally distributing the corrective and therapeutic force at each point at which the means for applying a corrective and therapeutic force is applied, said means for equally distributing the corrective and therapeutic force positioned juxtaposed and having a longitudinal axis in parallel with a longitudinal axis of said means for applying a corrective and therapeutic force.

2. The improved osteoarthritis knee brace of claim 1, wherein the at least one pivoting hinge is chosen from the group consisting of uni-centric and polycentric pivoting hinges.

3. The improved osteoarthritis knee brace of claim 1, wherein the at least one vertical strut comprises a first and second vertical strut.

4. The improved osteoarthritis knee brace of claim 3, wherein:
   a) the shin cuff includes an anterior static portion and a posterior adjustable strap member for securing the shin cuff of the knee brace to the patient below the knee joint; and
   b) the thigh cuff includes a posterior static portion and an anterior adjustable strap member for securing the thigh cuff of the knee brace to the patient above the knee joint.

5. The improved osteoarthritis knee brace of claim 4, further comprising:
   a) an adjustable mid-thigh cuff strap positioned below the thigh cuff anterior adjustable strap member but above the knee joint and securable to itself; and
   b) an adjustable calf strap positioned above the shin cuff posterior adjustable strap member but below the knee joint and securable to itself.

6. The improved osteoarthritis knee brace of claim 5, further comprising:
   a) an adjustable thigh cushion pad attached along an inner surface of the mid-thigh cuff strap; and
   b) an adjustable calf cushion pad attached along an inner surface of the calf strap.

7. The improved osteoarthritis knee brace of claim 3, wherein the at least one pivoting hinge comprises two pivoting hinges, a first pivoting hinge intermediately disposed between upper and lower portions of the first vertical strut and a second pivoting hinge intermediately disposed between upper and lower portions of the second vertical strut.

8. The improved osteoarthritis knee brace of claim 7, wherein a uni-centric pivoting hinge is employed along the first vertical strut and a polycentric hinge is employed along the second vertical strut.

9. The improved osteoarthritis knee brace of claim 7, wherein the first vertical strut upper portion is posteriorly offset as compared to the second vertical strut upper portion.

10. The improved osteoarthritis knee brace of claim 9, wherein the offset is between 10 and 20 degrees from a center axis of the first vertical strut.

11. The improved osteoarthritis knee brace of claim 1, wherein the forces of the means for applying a corrective and therapeutic force are chosen from the group consisting of varus and valgus forces.

12. The improved osteoarthritis knee brace of claim 1, wherein the knee brace is configurable for either a left or right knee.

13. The improved osteoarthritis knee brace of claim 1, further comprising means for providing gait kinetic swing-assistance.

14. The improved osteoarthritis knee brace of claim 13, wherein the means for providing gait kinetic swing-assistance is a spring-biased mechanism mounted along the at least one pivoting hinge.

15. The improved osteoarthritis knee brace of claim 13, wherein the means for providing gait kinetic swing-assistance is an adjustable dynamic fulcrum mounted on an outer surface of the at least one pivoting hinge.

16. The improved osteoarthritis knee brace of claim 15, wherein the adjustable dynamic fulcrum comprises an elastic member positioned over at least one setting block.

17. The improved osteoarthritis knee brace of claim 15, wherein the at least one pivoting hinge is a polycentric hinge.

18. The improved osteoarthritis knee brace of claim 1, wherein the means for applying a corrective and therapeutic force to the osteoarthritis damaged knee joint is at least one inflatable bladder system.

19. The improved osteoarthritis knee brace of claim 18, wherein:
   a) the at least one vertical strut comprises a first and second vertical strut;
   b) the at least one pivoting hinge comprises a uni-centric hinge and a polycentric hinge; and
   c) the at least one inflatable bladder system comprises a plurality of bladder systems.

20. The improved osteoarthritis knee brace of claim 19, wherein the plurality of bladder systems comprises upper and lower bladder systems employed in a plurality of different bladder system set-ups chosen from the group consisting of:
   a) an upper bladder system mounted on an inner surface of the polycentric hinge and a lower bladder system mounted on an inner surface of a first lower upright member positioned below the polycentric hinge;
   b) an upper bladder system mounted on the inner surface of the polycentric hinge and a lower bladder system mounted on an inner surface of a second lower upright member positioned below the uni-centric hinge;
   c) an upper bladder system mounted on an inner surface of the uni-centric hinge and a lower bladder system mounted on an inner surface of a second lower upright member positioned below the uni-centric hinge;
   d) an upper bladder system mounted on an inner surface of the uni-centric hinge and a lower bladder system mounted on an inner surface of a first lower upright member positioned below the polycentric hinge;
   e) two upper bladder systems, one each mounted on inner surfaces of each of the uni-centric and polycentric hinges and two lower bladder systems, one each mounted on inner surfaces of first and second lower upright members positioned below the uni-centric and polycentric hinges;
   f) two upper bladder systems, one each mounted on inner surfaces of each of the uni-centric and polycentric hinges and one lower bladder system mounted on an inner surface of a first lower upright member positioned below the uni-centric hinge;
   g) two upper bladder systems, one each mounted on inner surfaces of each of the uni-centric and polycentric hinges and one lower bladder system mounted on an inner surface of a second lower upright member positioned below the polycentric hinge;
   h) two lower bladder systems, one each mounted on inner surfaces of first and second lower upright members positioned below the uni-centric and polycentric hinges and one upper bladder system mounted on an inner surface of the polycentric hinge; and
   i) two lower bladder systems, one each mounted on inner surfaces of first and second lower upright members positioned below the uni-centric and polycentric hinges and one upper bladder system mounted on an inner surface of the uni-centric hinge.

21. The improved osteoarthritis knee brace of claim 18, wherein the at least one inflatable bladder system includes a pliable retaining pouch, an inflatable bladder unit having an inflation tube and nozzle and the means for equally distributing the corrective and therapeutic force at each point at which the means for applying a corrective and therapeutic force is applied.

22. The improved osteoarthritis knee brace of claim 21, wherein the means for equally distributing the corrective and therapeutic force at each point at which the means for applying a corrective and therapeutic force is applied comprises at least one insert unit enclosed within the inflatable bladder system retaining pouch.

23. The improved osteoarthritis knee brace of claim 22, wherein the at least one insert unit comprises a single insert unit positioned within the retaining pouch between the inflatable bladder unit and a side of the pouch that contacts an outer skin surface of the knee joint area, the single insert unit equally distributing the force of the inflatable bladder when air is introduced against the knee joint area and/or the lower leg based upon a total surface area thereof.

24. The improved osteoarthritis knee brace of claim 22, wherein the at least one insert unit is made from a rigid or semi-rigid material and its shape is chosen from the group consisting of planar, generally planar, concave, convex and anatomical.

25. The improved osteoarthritis knee brace of claim 1, further comprising at least one pliable hinge wrap for surrounding the at least one pivoting hinge and fabricated from a material with a coefficient of friction, sufficient to prevent brace slippage, located on an inner surface of the at least one pliable wrap, which comes into contact with an outer surface of the patient's skin.

26. An osteoarthritis knee brace for treating a knee joint and an area in proximity thereof of a patient affected with osteoarthritis of the knee, the osteoarthritis knee brace comprising:
   a) a pair of vertical upright strut members, each vertical upright strut member comprising an upper and lower portion;
   b) a pair of hinge members, one each disposed along one of the pair of vertical upright strut members at a generally middle portion thereof;
   c) a shin cuff attached at opposing ends thereof to the lower portions of the pair of vertical upright strut members and having an adjustable strap member for securing the shin cuff to the patient below the knee joint;
   d) a thigh cuff attached at opposing ends thereof to the upper portions of the pair of vertical upright strut members and having an adjustable strap member for securing the thigh cuff to the patient above the knee joint;
   e) means for applying a corrective and therapeutic force to the knee joint affected by the osteoarthritis and the lower leg portion located below said knee joint, said means removeably positionable about the osteoarthritis knee brace at the knee joint and along the lower leg portion along inner surfaces of the pair of vertical upright strut members and inner surfaces of the pair of hinge members such that the means for applying a corrective and therapeutic force makes direct contact with a side portion of the lower leg and the knee joint; and f) means for equally distributing the corrective and therapeutic force at each point at which the means for applying a corrective and therapeutic force is applied, said means for equally distributing the corrective and therapeutic force positioned juxtaposed and having a longitudinal axis in parallel with a longitudinal axis of said means for applying a corrective and therapeutic force.

27. The osteoarthritis knee brace of claim 26, wherein one of the pair of vertical upright strut member upper portions is angled backwardly.

28. The osteoarthritis knee brace of claim 27, wherein the backwardly angled vertical upright strut member upper portion is offset between 10 and 20 degrees from a vertical center axis of said vertical upright strut member.

29. The osteoarthritis knee brace of claim 26, wherein the means for applying a corrective and therapeutic force to the knee joint affected by the osteoarthritis and the lower leg portion located below said knee joint is at least one inflatable bladder system.

30. The osteoarthritis knee brace of claim 29, wherein the at least one inflatable bladder system comprises a plurality of bladder systems positionable at the knee joint area on one or both sides thereof, below the knee joint area along the lower leg portion on one or both sides thereof, at the knee joint area on one side and along the lower leg portion on an opposed side, at the knee joint area on both sides and along the lower leg portion on one of either two sides, along the lower leg portion on both sides and at the knee joint area on one of either two sides or at the knee joint and the lower leg portion on both sides thereof.

31. The osteoarthritis knee brace of claim 26, wherein the means for equally distributing the corrective and therapeutic force at each point at which the means for applying a corrective and therapeutic force is applied is at least one rigid or semi-rigid insert member enclosed within said means for applying a corrective and therapeutic force.

32. The osteoarthritis knee brace of claim 26, further comprising a pair of pliable wrap members, one each for surrounding the pair of hinges, each pliable wrap member having at least one surface area fabricated from a material with a coefficient of friction to assist in maintaining brace alignment, said material located on an inner surface of each pliable wrap member that comes into contact with an outer surface of the patient's skin.

33. The osteoarthritis knee brace of claim 26, configurable to treat either a left or right osteoarthritis effected knee joint.

34. The osteoarthritis knee brace of claim 26, further comprising a gait kinetic swing-assistance mechanism mounted along at least one of the pair of hinge members.

35. The osteoarthritis knee brace of claim 26, further comprising an adjustable dynamic fulcrum mounted along at least one of the pair of hinge members with an elastic band attached to at least one of the pair of the hinge members, alternatively built into at least one of the pair of hinge members or attached to the upper and lower portions of at least one of the pair of the vertical upright strut members.

36. The osteoarthritis knee brace of claim 35, further comprising at least one setting block and the elastic band having at least one strength of the adjustable dynamic fulcrum for providing a multitude of varying swing assist forces to move the lower leg during gait kinetics.

* * * * *